United States Patent
Pierce et al.

(10) Patent No.: US 12,303,425 B2
(45) Date of Patent: May 20, 2025

(54) METHODS AND DEVICES TO PREVENT PREMATURE BIRTH, STILLBIRTH, MISCARRIAGE, INFECTION, OR PREGNANCY

(71) Applicant: NINE MEDICAL, INC., San Francisco, CA (US)

(72) Inventors: Ryan Kendall Pierce, Carl Junction, MO (US); Michael Schoof, San Francisco, CA (US)

(73) Assignee: Nine Medical, Inc., San Francisco, CA (US)

( * ) Notice: Subject to any disclaimer, the term of this patent is extended or adjusted under 35 U.S.C. 154(b) by 687 days.

(21) Appl. No.: 17/418,685

(22) PCT Filed: Dec. 27, 2019

(86) PCT No.: PCT/US2019/068806
§ 371 (c)(1),
(2) Date: Jun. 25, 2021

(87) PCT Pub. No.: WO2020/140075
PCT Pub. Date: Jul. 2, 2020

(65) Prior Publication Data
US 2022/0125621 A1    Apr. 28, 2022

Related U.S. Application Data

(60) Provisional application No. 62/785,697, filed on Dec. 28, 2018, provisional application No. 62/855,633, filed on May 31, 2019.

(51) Int. Cl.
*A61F 6/08*    (2006.01)
*A61F 5/455*   (2006.01)

(52) U.S. Cl.
CPC .............. *A61F 6/08* (2013.01); *A61F 5/4553* (2013.01)

(58) Field of Classification Search
CPC .... A61F 6/08; A61F 6/06; A61F 6/146; A61F 6/065; A61F 5/4553; A61F 5/455
(Continued)

(56) References Cited

U.S. PATENT DOCUMENTS

| RE20,061 E | 8/1936 | Kirk |
| 2,146,472 A | 2/1939 | Heintz et al. |

(Continued)

FOREIGN PATENT DOCUMENTS

| CN | 2785605 Y | 6/2006 |
| CN | 2917679 Y | 7/2007 |

(Continued)

OTHER PUBLICATIONS

JP 2003520071 A1 machine translation (Year: 2003).*

(Continued)

*Primary Examiner* — Caitlin A Carreiro
(74) *Attorney, Agent, or Firm* — Shay Glenn LLP

(57) ABSTRACT

Methods and devices to control movement of microorganisms, sperm or viruses within a female reproductive system, including methods and devices for preventing infection or pregnancy. Devices may include a cervical barrier that is configured to allow biological fluids to exit the uterus and cervical canal while preventing the ascension of microorganisms, sperm or viruses into the cervical canal and uterus.

20 Claims, 14 Drawing Sheets

(58) Field of Classification Search
USPC .............. 128/841, 834, 835, 832, 833, 839
See application file for complete search history.

(56) References Cited

U.S. PATENT DOCUMENTS

| | | | |
|---|---|---|---|
| 2,616,421 A * | 11/1952 | Greenberg | A61M 31/00 600/431 |
| 2,841,146 A | 7/1958 | Heuboski | |
| 3,107,671 A | 10/1963 | Farina et al. | |
| 4,322,463 A | 3/1982 | Goepp et al. | |
| 4,381,771 A * | 5/1983 | Gabbay | A61F 6/08 128/836 |
| 4,589,880 A * | 5/1986 | Dunn | A61F 6/08 604/93.01 |
| 4,770,167 A | 9/1988 | Kaali et al. | |
| 5,042,503 A | 8/1991 | Torok et al. | |
| 5,123,424 A | 6/1992 | Koch | |
| 5,301,680 A | 4/1994 | Rosenberg | |
| 5,510,064 A * | 4/1996 | Koch | A61F 6/12 264/222 |
| 5,637,877 A | 6/1997 | Sinofsky | |
| 5,980,804 A | 11/1999 | Koch | |
| 6,134,466 A | 10/2000 | Rosenberg | |
| 6,254,537 B1 | 7/2001 | Nguyen | |
| 6,350,463 B1 | 2/2002 | Herman et al. | |
| 6,375,970 B1 | 4/2002 | Bieniarz | |
| 6,526,980 B1 | 3/2003 | Tracy et al. | |
| 6,589,216 B1 | 7/2003 | Abbott et al. | |
| 7,763,059 B2 | 7/2010 | Perez | |
| 8,408,212 B2 | 4/2013 | O'Brien et al. | |
| 8,679,013 B2 | 3/2014 | Ziarno et al. | |
| 9,474,885 B2 | 10/2016 | Cline et al. | |
| 9,764,120 B2 | 9/2017 | Cline et al. | |
| 10,773,062 B2 | 9/2020 | Cline et al. | |
| 2002/0193670 A1 | 12/2002 | Garfield et al. | |
| 2003/0088217 A1 | 5/2003 | Bergeron et al. | |
| 2003/0212382 A1 | 11/2003 | Abbott et al. | |
| 2007/0255184 A1 | 11/2007 | Shennib | |
| 2007/0261699 A1 | 11/2007 | Callister et al. | |
| 2008/0082024 A1 | 4/2008 | Meyer et al. | |
| 2009/0076340 A1 | 3/2009 | Libbus et al. | |
| 2010/0331739 A1 | 12/2010 | Maltz et al. | |
| 2011/0237972 A1 | 9/2011 | Garfield et al. | |
| 2012/0035508 A1 | 2/2012 | Van Leer | |
| 2012/0265090 A1 | 10/2012 | Fink et al. | |
| 2013/0053657 A1 | 2/2013 | Ziarno et al. | |
| 2013/0197324 A1 | 8/2013 | Waterhouse et al. | |
| 2013/0211384 A1 | 8/2013 | Raspagliesi | |
| 2013/0281861 A1 | 10/2013 | Flomerfelt et al. | |
| 2014/0135587 A1 * | 5/2014 | Hess | A61B 17/4241 606/119 |
| 2014/0180169 A1 | 6/2014 | Peters et al. | |
| 2014/0210640 A1 | 7/2014 | Rahman et al. | |
| 2014/0278229 A1 | 9/2014 | Hong et al. | |
| 2016/0120435 A1 | 5/2016 | Young | |
| 2016/0157717 A1 | 6/2016 | Gaster | |
| 2016/0262649 A1 | 9/2016 | Hayes-Gill et al. | |
| 2016/0331299 A1 | 11/2016 | Cline et al. | |
| 2018/0296156 A1 | 10/2018 | Penders et al. | |
| 2020/0146614 A1 | 5/2020 | Cline et al. | |
| 2020/0360674 A1 | 11/2020 | Cline et al. | |
| 2022/0287624 A1 | 9/2022 | Cline et al. | |

FOREIGN PATENT DOCUMENTS

| | | | |
|---|---|---|---|
| CN | 201783070 U | 4/2011 | |
| JP | S5812657 A | 1/1983 | |
| JP | 2002512180 A | 4/2002 | |
| JP | 2002515069 A | 5/2002 | |
| JP | 2003520071 A * | 7/2003 | |
| JP | 2007508907 A | 4/2007 | |
| JP | 2012165787 A | 9/2012 | |
| JP | 2014116754 A | 6/2014 | |
| WO | WO00/06022 A1 | 2/2000 | |
| WO | WO2001/021116 A1 | 3/2001 | |
| WO | WO2007/130958 A2 | 11/2007 | |
| WO | WO2012/129304 A2 | 9/2012 | |
| WO | WO2020/140075 A1 | 7/2020 | |

OTHER PUBLICATIONS

Pierce et al.; U.S. Appl. No. 18/478,290 entitled "Methods and devices to prevent premature birth," filed Sep. 29, 2023.

Becher et al.; The cervical mucus plug: Structured review of the literature; Acta Obstetricia et Gynecologica; 88(5); pp. 502-513; May 2009.

Graczyk et al.; Analysis of abdominal electrical activity of uterus-approximate entropy appoarch; IEEE, 22nd Annual EMBS International Conference, Chicago, IL; pp. 1352-1355; Jul. 23-28, 2000.

Heard et al.; Silk-based injectable biomaterial as an alternative to cervical cerclage: An in vitro study; Reproductive Sciences; 20(8); pp. 929-936; Aug. 2013.

Saling et al.; Role of operative early total cervix occlusion for prevention of late abortion and early prematurity; Proc. of the 5th World Congress of Perinatal Medicine; Barcelona, Spain; pp. 602-607; Sep. 23, 2001.

Sciscione et al.; Intracervical fibrin sealants: A potential treatment for early preterm permature rupture of the membranes; Am J Obstet Gynecol; 184(3); pp. 368-373; Feb. 2001.

Firth-Cozens; Interventions to improve physicians' well-being and patient care; Social Science and Medicine; 52(2); pp. 215-222; Jan. 2001.

* cited by examiner

   
FIG. 3J    FIG. 3K    FIG. 3L    FIG. 3M
  
FIG. 3N    FIG. 3O    FIG. 3P
 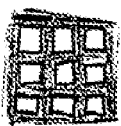 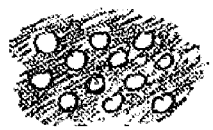 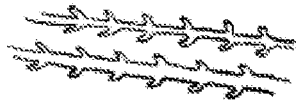
FIG. 3Q    FIG. 3R    FIG. 3S    FIG. 3T
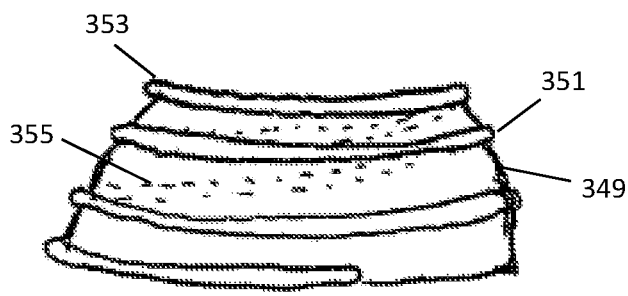
FIG. 3U

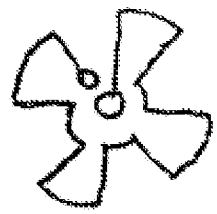
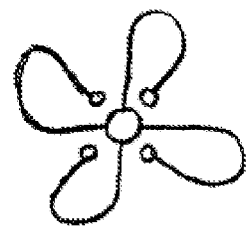
FIG. 5A  FIG. 5B  FIG. 5C
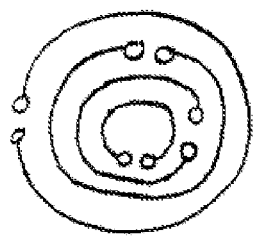
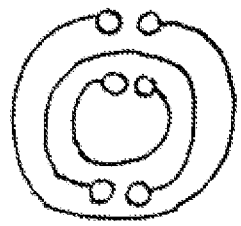
FIG. 5D  FIG. 5E  FIG. 5F
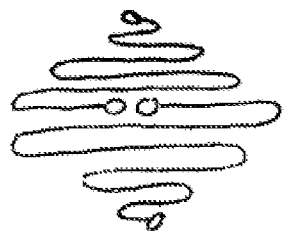
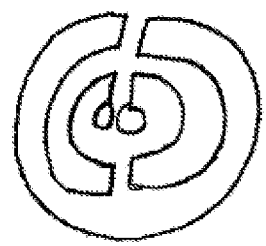
FIG. 5G  FIG. 5H  FIG. 5I
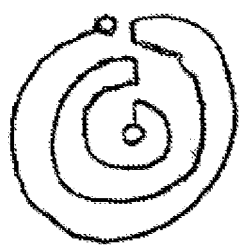
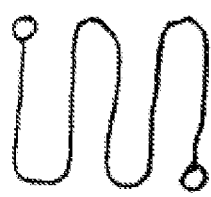
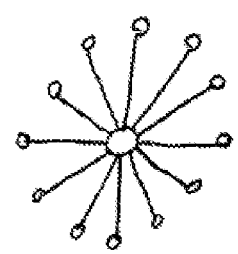
FIG. 5J  FIG. 5K  FIG. 5L Vaginal end ←     Cervical end →

801

METHODS AND DEVICES TO PREVENT PREMATURE BIRTH, STILLBIRTH, MISCARRIAGE, INFECTION, OR PREGNANCY

CROSS REFERENCE TO RELATED APPLICATIONS

This application claims priority to U.S. Provisional Patent Application No. 62/785,697, entitled "METHODS AND DEVICES TO PREVENT PREMATURE BIRTH, STILLBIRTH, MISCARRIAGE, INFECTION OR PREGNANCY," filed on Dec. 28, 2018; and to U.S. Provisional Patent Application No. 62/855,633, entitled "METHODS AND DEVICES TO PREVENT PREMATURE BIRTH, STILLBIRTH, MISCARRIAGE, INFECTION OR PREGNANCY," filed on May 31, 2019, each of which is herein incorporated by reference in its entirety.

This application may be related to U.S. patent application Ser. No. 14/992,914, now U.S. Pat. No. 9,474,885, entitled "METHODS AND DEVICES TO PREVENT PREMATURE BIRTH," filed on Jan. 11, 2016; and to U.S. patent application Ser. No. 15/112,698, entitled "DEVICES AND METHODS FOR MONITORING PREGNANCY," filed on Jan. 31, 2015, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The methods and apparatuses described herein generally relate to the prevention of premature birth, pregnancy and/or infection by providing a cervical barrier. For example, described herein are methods and apparatuses for forming a barrier preventing passage of sperm or microorganisms into the uterus while allowing passage of egressing materials from the uterus.

BACKGROUND

The migration of cellular organisms, viruses, or their byproducts from the vagina to the cervix or uterus can create a number of unwanted effects. For example, premature birth, a leading cause of neonatal death and disability with adverse health effects that can last into adulthood, is frequently caused by intra-amniotic infection. Microorganisms migrating, relocating, proliferating, or otherwise moving from or through the vagina and/or cervical canal may eventually invade the amniotic cavity, and can cause the release of cytokines, which fight infection but cause inflammation, which releases prostaglandins. These, in turn, may cause biochemical processes that lead to contractions and cervical dilation and in turn, premature birth. Exposure of cervical tissue to pathogenic bacteria or its byproducts may cause inflammation or cervical remodeling, which may lead to premature birth. Infections originating in the vagina may also cause miscarriage and stillbirth. An unwanted pregnancy itself is a result of ascension of spermatozoa from the vagina, through the cervical canal, to the uterus and ultimately to the ovum.

Therefore, devices and methods that minimize or prevent the movement of some or all cellular organisms, viruses, or their byproducts from the vagina to the cervix or uterus may address a number of clinical needs.

SUMMARY

Described herein are apparatuses (e.g., systems and devices, including cervical caps) and methods for controlling the movement of sperm, cellular organisms, viruses, or their byproducts from the vagina to the cervix or uterus. In general, the devices can be configured to be inserted into the vagina and cover at least a portion of the cervix or the entrance into the cervical canal. These apparatuses may include a first structure or region that presses on the vaginal wall, ectocervix, or both in order to maintain position and/or create a barrier for migration, relocation, proliferation, or movement of cellular organisms, microbes, bacteria, viruses, fungi, spermatozoa ("sperm"), or their byproducts along a path toward the cervical canal or a surface of the ectocervix. Alternatively or additionally, theses apparatuses may include a second structure or region that covers part or all of the ectocervix or inferior (external) opening of the cervical canal that allows material egressing from the cervix to travel through the channel toward the vagina while preventing material (and in particular motile organisms, such as sperm and motile pathogens including bacteria) ascending the vagina towards the cervix from reaching the cervical canal.

For example, the apparatuses can include one or more open channels including grooves, protrusions, rings, and other features designed to direct the sperm and/or cellular organisms, viruses, etc. away from the cervical canal. The devices can alternatively or additionally include one or more channels that allow egressing material, such as blood, mucus, etc. to pass out of the uterus and/or cervical canal. In some variations these apparatuses may be configured to seal to the external os of the cervix by including a plurality of protrusions (e.g., rings, spirals (including helical spirals), etc.) arranged to prevent migration of the sperm and/or microorganisms (e.g., bacteria, virus, yeast, etc.) from passing between the apparatus and the external os into the cervical canal.

According to some embodiments, a contraceptive cervical cap includes: a dome region configured to fit over the external os of the cervix, the dome region having a channel configured to allow egressing fluid from the external os to travel in a distal direction toward the lower vagina, the channel configured to direct the egressing fluid entering a cervical side of the dome region to pass through the channel and out a vaginal side of the dome region, wherein the channel is configured to prevent sperm entering the vaginal side of the dome region from exiting a cervical side of the dome region. The channel can wind around at least a portion of a central axis of the dome region. The channel can radiate from a central axis of the dome region. The channel can have a diameter of about 100 micrometers to 4 millimeters. The channel can have a diameter of about 500 micrometers to 2.5 millimeters. The channel can have a length of 2 to 2500 millimeters. The channel can have a length of 10 to 300 millimeters. The channel can include an inner wall having one or more redirecting features configured to direct the sperm back toward the lower vagina, direct the sperm to a holding area of the channel, or direct the sperm back toward the lower vagina and direct the sperm to a holding area of the channel. The channel can define a central path for the egressing fluid to travel in the distal direction. The channel can include a series of redirecting features that form a ratcheting arrangement that progressively directs the sperm away from the central path. For example, in some variations wall transitions into redirecting features may be abrupt; in some variations, wall transitions may be gradual, for example, having a radius of curvature of about 150 micrometers or greater, to guide wall-tracking sperm. For example, a sperm may generally track along a wall that is straight, curves toward it (i.e., into its path), or curves gently away. If the wall curves abruptly away, at a radius of curvature of about 150 microns or less, the sperm may continue straight, rather than continue to track along the wall. Thus, in some variations the redirecting features may be configured to guide sperm in a direction that is in a distal direction (e.g., in the central channel), back towards the vaginal side of the apparatus. In general, the wall(s) of the redirecting features may be configured to steer sperm or other motile microorganisms in this distal direction. For example, a distal-most wall of the channel or redirecting feature may have a radius of curvature that is 150 microns or less. In some variations, the one or more redirecting features can extend 50 microns or more (e.g., 50 microns to 1.5 mm) from the main channel. The channel can include one or more valves that preferentially allows fluid to flow or travel in the distal direction. The one or more valves can be within the channel between a first port at the cervical side of the dome region and a second port at the vaginal side of the dome region. The one or more valves can be at a first port at the cervical side of the dome region or at the second port at the vaginal side of the dome region. An inner wall of the channel can include micropillars or nanopillars configured to prevent migration sperm to a cervical end of the channel at the cervical side of the dome region. The cervical cap can include an outer interface surface configured to press against one or both of the vaginal wall and the ectocervix, wherein the outer interface surface has one or more protruding features configured to concentrate force on one or both of the vaginal wall and the ectocervix at the one or more protruding features, thereby providing a seal barrier to migration of sperm between the outer interface surface and one or both of the vaginal wall and the ectocervix.

According to some embodiments, a contraceptive device includes: a cervical cap configured to fit over the external os of the cervix, the cervical cap including an outer interface surface configured to press against one or both of the vaginal wall and the ectocervix, wherein the outer interface surface has a convex surface with one or more protruding features configured to concentrate force on one or both of the vaginal wall and the ectocervix at the one or more protruding features, thereby providing a barrier to migration of sperm into the external os between the outer interface surface and one or both of the vaginal wall and the ectocervix. The one or more protruding features can form one or more protruding ring structures or one or more protruding spiral structures (including helical spirals) around the outer interface surface. The one or more protruding features can form one or more protruding spiral structures around the outer interface surface, wherein the outer interface surface further comprises a circumferentially complete ridge around a dome region of the cervical cap that covers the external os. The cervical cap can include a dome region configured to fit over the external os of the cervix, the dome region having a channel configured to allow egressing fluid from the external os to travel through the channel in a distal direction and out a vaginal side of the dome region, wherein the channel includes at least a portion that runs non-parallel to the distal direction and is configured to prevent sperm entering the vaginal side of the dome region from exiting a cervical side of the dome region. The channel can have a length of 2 to 2500 millimeters. The channel can have a length of 10 to 300 millimeters. The outer interface surface can further include micropillars or nanopillars configured to prevent migration of sperm between the outer interface surface and one or both of the vaginal wall and the ectocervix.

According to some embodiments, the device is a pessary device that includes: a dome region configured to fit over the external os of the cervix, the dome region having a channel configured to allow egressing fluid from the external os to travel through the channel out a vaginal side of the dome region in a distal direction, wherein the channel includes at least portion that runs non-parallel to the distal direction and is configured to prevent microorganisms or viruses entering the vaginal side of the dome region from exiting a cervical side of the dome region. The device can include an outer interface surface configured to press against one or both of the vaginal wall and the ectocervix, wherein the outer interface surface has one or more protruding features configured to concentrate force on one or both of the vaginal wall and the ectocervix at the one or more protruding features, thereby providing a barrier to migration of microorganisms or viruses between the outer interface surface and one or both of the vaginal wall and the ectocervix. The outer interface surface can further include micropillars or nanopillars configured to prevent migration of sperm between the outer interface surface and one or both of the vaginal wall and the ectocervix. The channel can have a diameter of about 100 micrometers to 4 millimeters. The channel can have a diameter of about 500 micrometers to 2.5 millimeters. The channel can have a length of 2 to 2500 millimeters. The channel can have a length of 10 to 300 millimeters. The channel can include an inner wall having one or more redirecting features configured to direct the sperm or microorganisms or viruses back toward the vagina, direct the sperm or microorganisms or viruses to a holding area of the channel, or direct the sperm or microorganisms or viruses back toward the vagina and direct the sperm or microorganisms or viruses to a holding area of the channel. The channel can define a central path for the egressing fluid to travel in the distal direction. The channel can include a series of redirecting features that form a ratcheting arrangement that progressively directs the sperm or microorganisms or viruses away from the central path. As mentioned above, wall transitions into redirecting features may be abrupt, or may be gradual, for example, having a radius of about 150 micrometers or greater, to guide wall-tracking sperm or microorganisms into the feature. The one or more redirecting features can extend 50 microns to 1.5 mm from the main channel. The channel can include one or more valves that preferentially allows fluid to flow travel in the distal direction. The one or more valves can be within the channel between a first port at the cervical side of the dome region and a second port at the vaginal side of the dome region. The one or more valves can be at a first port at the cervical side of the dome region or at the second port at the vaginal side of the dome region. An inner wall of the channel can include micropillars or nanopillars configured to prevent migration of sperm to a cervical end of the channel at the cervical side of the dome region.

According to some embodiments, a method of using a device as described herein (e.g., a pessary device) includes: positioning a dome region of the pessary device over the external os of the cervix, the dome region having a channel configured to allow egressing fluid from the external os to travel through the channel out a vaginal side of the dome region in a distal direction, wherein the channel includes at least portion that runs non-parallel to the distal direction and is configured to prevent microorganisms or viruses entering the vaginal side of the dome region from exiting a cervical side of the dome region; and shining the antimicrobial light on the pessary device such that the antimicrobial light shines through a thickness of the pessary device to kill the microorganisms or viruses within the channel. Shining the antimicrobial light on the pessary device can kill sperm within the channel. Shining the antimicrobial light on the pessary device can include activating a light source within or on the pessary device.

The devices described herein can be manufactured using any of a number of techniques. For example, the devices (or portions of the devices) can be three-dimensional (3D) printed, injection molded, cured, and/or etched. In some cases, the channel is formed using a machined dissolvable part matching the channel profile, which is embedded in the device material, then dissolved away.

For example, described herein are cervical caps that include: a dome region configured to fit over the external os of the cervix, the dome region having an open channel configured to allow fluid from the external os to travel in a first direction through the channel toward the lower vagina and out of a vaginal side of the dome region, wherein the shape of the open channel is configured to prevent sperm or microorganisms from entering the vaginal side of the dome region from exiting the open channel out of a cervical side of the dome region.

As mentioned, in general, the shape of the open channel (or channels, where more than one channel is included) may form a conduit having a wall shape that directs sperm or microorganisms traveling in the open channel from the vaginal side of the dome region to travel in the first direction back towards the vaginal side of the dome region. For example, the shape of the open channel may comprise a plurality of enlargements, recesses, projections, baffles, ramps, turnarounds, cavities, or buckets which direct sperm or microorganisms to travel in the first direction back towards the vaginal side of the dome region. In some variations, the shape of the open channel provides a resistance to fluid flow through the open channel in the first direction that is 10 fold or greater lower than the resistance to fluid flow through the open channel in a second direction that is opposite to the first direction.

In some variations, the open channel comprise a wall shape that includes a plurality of curved portions that communicate with a central passage through the open channel at an acute angle relative to the first direction so that flow off of the curved portions has a component of flow in the first direction. The general trajectory of flow (and/or of movement of a motile sperm or other organism) along the curved portion points in the first direction or forms an acute angle with a first direction so that the motile sperm of other organism is re-directed back towards the vaginal side of the device (e.g., in the first direction).

Thus, in some variations, the open channel includes a wall having one or more redirecting features configured to direct the sperm or microorganisms to travel in the first direction back towards the vaginal side of the dome region. The open channel may define a central path for the fluid to travel in the first direction. The wall may include a series of redirecting features that form a ratcheting arrangement that progressively directs the sperm or microorganisms away from the central path. Wall transitions into redirecting features may be abrupt, or may be gradual, for example, having a radius of about 150 micrometers or greater to guide wall-tracking sperm into the feature. The one or more redirecting features can extend 50 microns to 1.5 mm from the main channel.

In some variations, the wall of the open channel may include micropillars or nanopillars configured to prevent migration of sperm or microorganisms through the open channel to the cervical side of the dome region.

In general, the open channel may extend from the vaginal side of the apparatus to the cervical side of the apparatus. The open channel may extend directly (e.g., along the central axis of the apparatus). In some variations the open channel winds around at least a portion of a central axis of the dome region. The open channel may radiate from a central axis of the dome region. In some variations the open channel has a diameter of about 100 micrometers to 4 millimeters; this diameter may be an average diameter or in some variations a minimum diameter. For example, the open channel may have a diameter of between about 500 micrometers to 2.5 millimeters (e.g., an average diameter or in some variation a minimum diameter). The open channel may have a length of between about 2 to 2500 millimeters. The open channel may have a length of between about 10 to 300 millimeters.

As mentioned, any of these apparatuses may have an outer interface surface configured to seal against one or both of the vaginal wall and the ectocervix, wherein the outer interface surface has one or more protruding features configured to concentrate force on one or both of the vaginal wall and the ectocervix at the one or more protruding features, thereby providing a barrier to migration of sperm or pathogen (e.g., microorganisms, virus, etc.) between the outer interface surface and one or both of the vaginal wall and the ectocervix.

For example, described herein are contraceptive devices, comprising: a cervical cap configured to fit over the external os of the cervix, the cervical cap including an outer interface surface configured to press against one or both of the vaginal wall and the ectocervix, wherein the outer interface surface has a convex surface with one or more protruding features configured to concentrate force on one or both of the vaginal wall and the ectocervix at the one or more protruding features, thereby providing a barrier to migration of sperm into the external os between the outer interface surface and one or both of the vaginal wall and the ectocervix.

As mentioned, the one or more protruding features may form one or more protruding ring structures or one or more protruding spiral structures around the outer interface surface. The one or more protruding features may form one or more protruding spiral structures around the outer interface surface, wherein the outer interface surface further comprises a circumferentially complete ridge around a dome region of the cervical cap that covers the external os.

Any of these cervical caps may include one or more open channels configured to allow fluid to flow in a first direction from the external os through the open channel and out a vaginal side of the cap, wherein the open channel is configured to prevent sperm entering the open channel from the vaginal side of the cap from exiting out of a cervical side of the cap.

Any of these apparatuses may be configured as a pessary device. For example a pessary device may include: a dome region configured to fit over the external os of the cervix, the dome region having an open channel configured to allow fluid flow from the external os to travel through the open channel in a first direction and out a vaginal side of the dome region, wherein the open channel is configured to prevent pathogens entering the vaginal side of the dome region from exiting a cervical side of the dome region. The open channel may comprise a wall shape that comprises a plurality of curved portions that communicate with a central passage through the open channel at an acute angle relative to the first direction so that flow off of the curved portions has a component of flow in the first direction. The open channel may include an inner wall having one or more redirecting features configured to direct the microorganisms or viruses back toward the vagina, direct the microorganisms or viruses to a holding area of the channel, or direct the microorganisms or viruses back toward the vagina and direct the microorganisms or viruses to a holding area of the channel. As mentioned, the open channel may define a central path for the egressing fluid to travel in the distal direction.

Also described herein are methods of using any of these devices. For example, described herein are methods of using a cervical cap. These methods may be methods of contraception. In some variations these methods may be methods of preventing infection. For example, a method may include: positioning a dome region of the cervical cap over the external os of the cervix so that an open channel through the dome region allows fluid to pass from the external os, through the open channel and out a vaginal side of the dome region in a first direction; and redirecting sperm or microorganisms that enter the open channel from the vaginal side of the dome region back out of the open channel on the vaginal side of the dome region by guiding the sperm or microorganisms against a wall shape of the open channel.

In general, the wall shape of the open channel may comprise a plurality of enlargements, recesses, projections, baffles, ramps, turnarounds, cavities, or buckets which direct sperm or microorganisms to travel in the first direction back towards the vaginal side of the dome region. In some variations the wall shape of the open channel may be configured to provide a resistance to fluid flow through the open channel in the first direction that is 10 fold or greater lower than the resistance to fluid flow through the open channel in a second direction that is opposite to the first direction.

Alternatively or additionally, the wall shape of the open channel may comprise a plurality of curved portions that communicate with a central passage through the open channel at an acute angle relative to the first direction so that flow off of the curved portions has a component of flow in the first direction. The wall shape of the open channel may comprise one or more redirecting features configured to direct the sperm or microorganisms to travel in the first direction back towards the vaginal side of the dome region. The wall shape of the open channel may comprise a series of redirecting features that form a ratcheting arrangement that progressively directs the sperm or microorganisms away from the central path.

As mentioned above, in some (but not all) variations, these methods may include shining a light (e.g., an antimicrobial light) on the cervical cap to illuminate the cervical cap and/or regions of the tissue adjacent to the cervical cap, such that the light shines through a thickness of the cervical cap to kill the sperm or microorganisms within the open channel. Illuminating the cervical cap in this manner may kill sperm within the channel. In some variations illuminating the cervical cap includes activating a light source within or on the cervical cap. The light may generally be one or more wavelengths of light that are known to be anti-sperm and/or anti-microbial (e.g., ultraviolet light). In any of these variations, the apparatus and/or method may be used with a chemical agent (e.g., a spermicide, anti-bacterial, antifungal, etc.); this agent may be applied on or in the apparatus. In some variations, the barrier may itself be antimicrobial, e.g., contain an antimicrobial agent, such as an antibiotic, that may be embedded on or within the barrier. An antimicrobial may therefore be released in a highly localized and controlled manner.

Any of these methods may include sealing an outer interface surface of the cervical cap to the external os of the cervix. For example, sealing may include concentrating force on one or both of the vaginal wall and the ectocervix at one or more protruding features, thereby providing a barrier to migration of sperm or microorganisms into the external os between the outer interface surface and one or both of the vaginal wall and the ectocervix. The one or more protruding features form one or more protruding ring structures or one or more protruding spiral structures around the outer interface surface.

The methods and devices described can affect the types, proportions, quantities, distributions, proliferation, migration, location, relocation, proliferation, movement, viability or survival of microorganisms, viruses, spermatozoa, fungi, or biological materials within a female reproductive system. In some embodiments, the devices prevent premature birth, stillbirth, miscarriage, infection, or pregnancy.

These and other features and advantages are described herein.

BRIEF DESCRIPTION OF THE DRAWINGS

Novel features of embodiments described herein are set forth with particularity in the appended claims. A better understanding of the features and advantages of the embodiments may be obtained by reference to the following detailed description that sets forth illustrative embodiments and the accompanying drawings.

FIGS. 5A-5N illustrate aerial views of various additional example channels.

DETAILED DESCRIPTION

Figure 1:
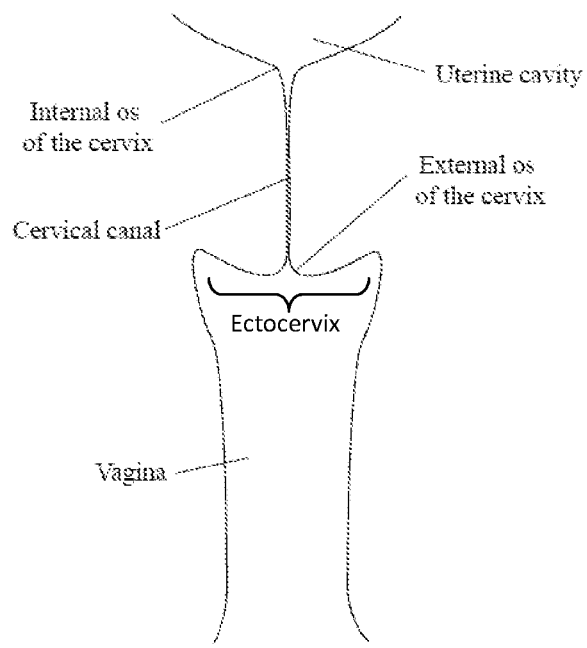
FIG. 1 illustrates the anatomy associated with the human female reproductive system as referred to herein.

Described herein are apparatuses (e.g., system, devices, etc.) and methods for controlling the movement of sperm, cellular organisms, viruses, or their byproducts from the vagina to the cervix or uterus. In general, the apparatus can be configured to be inserted into the vagina and cover at least a portion of the cervix or the entrance into the cervical canal. The apparatus can include one or more open channels, grooves, protrusions, rings, and other features designed to direct the sperm, cellular organisms, viruses, etc. away from the cervical canal. The apparatus can further include features that allow egressing material, such as blood, mucus, etc. to pass out of the uterus and/or cervical canal.

In particular, the apparatuses described herein can include one or more open channels formed and/or embedded within the apparatus that allow egressing material to flow through the device from the cervical side of the device to the vaginal side of the device, while preventing the passage of material, and in particular of motile organisms such as sperm and/or microorganisms (bacteria, etc.), viruses, etc. The channel(s) may wind in one or more circuitous paths within the device to provide a longer path for ascending sperm, organisms, viruses, etc. to travel, thereby reducing the probability of such ascending material reaching the entrance to the cervical canal. In some examples, the inner walls of the channel(s) include a surface pattern designed to redirect the ascending sperm, organisms, viruses, etc. in directions away from the entrance to the cervical canal. In some cases, the surface patterns direct the ascending material back toward the lower vagina.

In some variations, the channel(s) may include one or more check valves that preferentially allow egressing material to flow toward the vagina while preventing ascending material from reaching the cervical opening. These check valves may be "always open" valves, such as tesla valves, that have a greater resistance to flow in one direction (e.g., from the vagina to the cervix) than in the other direction (e.g., from the cervix to the vagina), such a 5-fold or greater resistance, a 10-fold or greater resistance, a 15-fold or greater resistance, a 20-fold or greater resistance, a 30-fold or greater resistance, a 50-fold or greater resistance, etc.

In any of these apparatuses an exterior surface of the device that contacts the ectocervix and/or vaginal wall may have ridges and/or grooves that create a seal with the ectocervix/vaginal wall, thereby providing a barrier to sperm, organisms, viruses, etc.

It should be understood that the inventions, embodiments, characteristics, and purposes described herein might be used in combination with one another.

The terms "egressing material" or "egressing materials", or variations thereof, as used herein should be understood to include, but are not limited to: blood, mucus, transudate, amniotic fluid, leukorrhea, lochia, uterine tissue, materials associated with menstruation, placental tissue, fetal tissue, cells, bacteria, or other liquids, gases, or other matter that might travel from a first site in a female reproductive system to a second site in a female reproductive system (for example, from a uterus to the vagina). The egressing materials, in many examples, would travel from a site within the cervical canal to a site in a vagina in the absence of any device placed in a female reproductive system.

The terms "introduced effect", "introduced effects", or variations thereof, as used herein, should be understood to include, without limitation, effects on cellular organisms, bacteria, microbes, viruses, fungi, spermatozoa, or their byproducts caused by one or more described attributes, elements, components, actions, or design features or provided by the invention; the attributes, elements, components, actions or design features include but are not limited to: light (including light of a particular wavelength, duration, intensity, and/or pattern of delivery), including light that damages, kills, causes not to reproduce, immobilizes, attracts, or repels targeted bacteria, microbes, viruses, fungi, spermatozoa, or their byproducts; blue light (including blue light of a particular wavelength, duration, intensity, and/or pattern of delivery), including blue light that damages, kills, causes not to reproduce, immobilizes, attracts, or repels targeted bacteria, microbes, viruses, fungi, spermatozoa, or their byproducts; UV light (including UV light of a particular wavelength, duration, intensity, and/or pattern of delivery), including UV light damages, kills, causes not to reproduce, immobilizes, attracts, or repels targeted bacteria, microbes, viruses, fungi, spermatozoa, or their byproducts; antibacterial, bacteriostatic, antimicrobial, antiviral, antifungal, or spermicidal agents or materials (including particular concentrations, amounts, configurations, or combinations thereof), in configurations that include but are not limited to coatings, structures, fillers, and reservoirs; heat or cold, or a source of heat or cold; electrical charge, or a source of electrical charge; Acidity or alkalinity, or a source of acidity or alkalinity; a surface of a particular roughness or smoothness that affects targeted bacteria, microbes, viruses, fungi, spermatozoa, or their byproducts, for example a surface featuring micropillars, nanopillars, and/or other structures which impale, cause to stretch, trap, tangle, or otherwise damage at least part of a cell; a presence or absence of nutrients or gases (for example, an absence of oxygen); an adhesive surface to which bacteria, microbes, viruses, fungi, spermatozoa, or their byproducts become adhered, or which slows their movement to another site; collection or entrapment; diversion to a path, where exposure to an introduced effect occurs; diversion to a path that lengthens the path of migration required for the bacteria, microbes, viruses, fungi, spermatozoa, or their byproducts to reach one or more of the following: adjacency to the cervix; a surface of the cervix; the cervical canal; the uterus; the fallopian tubes; diversion toward a site in the vagina that is not adjacent a cervix.

In many cases, the terms "introduced effect", "introduced effects", or variations thereof, as used herein, refer to effects that destroy, kill, damage, neutralize, compromise, immobilize, collect, entrap, or cause not to reproduce, the following: bacteria, microbes, viruses, fungi, spermatozoa, or their byproducts.

It should be understood that terms such as "migration", "relocation", "proliferation", or "movement" may be used herein to generally describe the changing of a location of (a) one or more microbes, cellular organisms, bacteria, viruses, spermatozoa, fungi, or their byproducts; or (b) one or more types of microbes, cellular organisms, bacteria, viruses, spermatozoa, fungi, or their byproducts; or (c) a range or zone containing one or more types of microbes, cellular organisms, bacteria, viruses, spermatozoa, fungi, or their byproducts. The changing of location is in some cases caused by or indicated by reproduction or the changing of a boundary of a zone, region, or volume of colonization.

It should be understood that terms such as "microbe" may refer to a variety of cellular organisms, including but not limited to bacteria and spermatozoa.

It should be understood that terms such as "micropillars", "nanopillars", and "micropillars/nanopillars," may refer to a variety of densities or configurations of tiny structures of various shapes, girths, tapers, stiffnesses, heights, and cross-sections, which may impale, stretch, bend, trap, tangle, slow the migration of, or otherwise damage or adversely affect targeted bacteria, microbes, viruses, fungi, spermatozoa, or their byproducts, for example by impaling, stretching, bending, trapping, tangling, slowing the migration of, or otherwise damaging or adversely affecting at least part of a cell. Heights of these structures may typically be 10 nanometers to 3000 nanometers, and more likely 80 nanometers to 750 nanometers, and perhaps more likely still 100 nanometers to 600 nanometers. A variety of feature shapes may be used, but could include cylindrical, square, rectangular, pointed, sharp, conical, bent, curved, partly spherical, and rounded, or combinations of these. Feature thickness, and spacing between features may typically be of the same order of magnitude as feature height, and in some variations between 0.25× (one quarter) and 3× (three fold) the feature height. Dimensions such as feature height, feature diameter, and spacing between features may be selected to be on the same order of magnitude of dimensions such as length or width of targeted bacteria.

In general, the apparatuses (e.g., devices) described herein can be configured to cover or fit over at least a portion of the cervix, and specifically over the ectocervix of the cervix, including or surrounding the external os. As mentioned above, the barrier may cover the cervical opening and/or surround the cervical opening. The applied barrier may extend slightly into the cervix, but is typically excluded from the majority of the cervical canal (also referred to as the endocervical canal). FIG. 1 illustrates a schematic of the anatomy, showing a vagina and the ectocervix. The ectocervix is the vaginal portion of the cervix, which typically has a convex, elliptical shape and projects into the cervix between the anterior and posterior vaginal fornices. The ectocervix includes the external orifice of the uterus (external os) corresponding to a central cervical opening into the cervical canal, thereby connecting the cervical canal with the vaginal canal. A region of the ectocervix around the external os is a small, depressed, somewhat circular region on the rounded extremity of the vaginal portion of the cervix. As used herein, the ectocervix may include all of the vaginal-facing portion of the cervix, including the external os, up to the intersection with the walls of the vagina (the vaginal fornix). The size and shape of the ectocervix and the external os can vary according to age, hormonal state, and whether natural or normal childbirth has taken place. In women who have not had a vaginal delivery, the external os is generally relatively small and circular, and in women who have had a vaginal delivery, it generally has a slit-like shape. On average, the ectocervix is about 3 centimeters (cm) (about 1.2 inch) long and about 2.5 cm (about 1 inch) wide. Any of the devices described herein may be (or include a portion) configured and adapted to at least partially cover or enclose the ectocervix.

Figure 2:
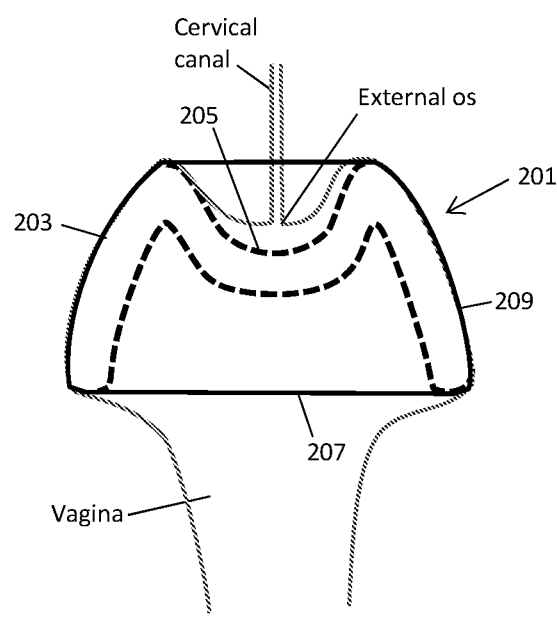
FIG. 2 illustrates an example device positioned over the ectocervix.

The devices described herein can be positioned partly or fully within a vagina and/or cervical canal, in order to prevent the migration, relocation, proliferation, or movement of cellular organisms, microbes, bacteria, viruses, fungi, spermatozoa, or their byproducts from a first location in the vagina to a second location in the vagina, cervix, cervical canal, uterus, or fallopian tube. In some embodiments, the device may fit over, around, near, or adjacent to the ectocervix, in a manner, for example, similar to a diaphragm or cervical cap. In some cases, the devices described herein may be referred to as a type of cervical cap or diaphragm. FIG. 2 illustrates an example device 201 positioned over the ectocervix. A dotted line represents an internal sectional view of the device fitting over the ectocervix, including the external os. A dome region 205 can correspond to an indented concave region of the device that is configured to cover at least a portion of the ectocervix including the external os. The dome region 205 can continuously connect to a brim portion 203 of the device, which is configured to press against the vaginal wall and/or against the ectocervix. In some embodiments, the brim portion has a concave surface. A distal edge 207 (relative to the cervix) of the device (e.g., of the brim portion) may be straight or be slanted. In some embodiments, the distal edge 207 curves radially inward. The device may or may not include a retriever, such as a strap or band, to facilitate removal of the device from the body.

In some embodiments, the device is held in place, in part or whole, by pressing against a region of the vaginal wall and/or pressing against the ectocervix, in a manner, for example, similar to a diaphragm or cervical cap. For example, an outer interface surface (e.g., 209) of the device can press against the vaginal wall and/or against the cervix (against the ectocervix and/or external os). In the example device of FIG. 2, the outer interface surface is on an exterior surface of the brim 203 configured to press against the vaginal wall and/or against the ectocervix. The central axis of the device shown in FIG. 2 is parallel with the long axis of the cervical canal. The outer interface surface of the device and the vaginal wall and/or ectocervix can act as a barrier to the migration, relocation, proliferation, or movement of cellular organisms, microbes, bacteria, viruses, fungi, spermatozoa, or their byproducts from a first location in the vagina to a second location in the vagina, cervix, cervical canal, uterus, or fallopian tube. In some embodiments, an antimicrobial, antiviral, or spermicidal substance is placed in or on one or more regions or surfaces of the device, where it contacts one or more of, or in some embodiments none of, the vaginal wall, endocervix, or ectocervix.

In some embodiments, at least a portion of the device that contacts a sexual partner of the wearer of the device during sexual activity is configured or constructed, by virtue of its shape, compliance, or coefficient of friction, to minimize or eliminate detection of the device by or discomfort to the sexual partner or the wearer of the device. In some embodiments, a portion of the device that contacts the sexual partner during sexual activity is comprised of or coated with one or more of the following materials: PTFE, expanded PTFE, polyimide, polyetheretherketone (PEEK), polyphenylene sulfide (PPS), polybutylene terephthalate (PBT), nylon, acetal, copolymer acetal, homopolymer acetal, polyester, polyphthalamide (PPA), thermoplastic polyimide (TPI), and/or a hydrogel.

In some embodiments, the device includes a first structure or region (e.g., 209 and/or 203) that presses on the vaginal wall, ectocervix, or both in order to maintain position and/or create a barrier for migration, relocation, proliferation, or movement of cellular organisms, microbes, bacteria, viruses, fungi, spermatozoa, or their byproducts along a path toward the cervical canal or a surface of the ectocervix, and a second structure or region (e.g., 205) that covers part or all of the ectocervix or inferior opening of the cervical canal, in some embodiments comprised of a porous, compliant material, such as expanded PTFE.

One or more surfaces of the device may include one or more surface features such as ridges, contours, grooves, and/or features, to increase the effective distance over which cellular organisms, microbes, bacteria, viruses, fungi, spermatozoa, or their byproducts must migrate, relocate, proliferate, or move in order to reach the cervix, cervical canal, or uterus from the vagina. For example, the outer interface surface (e.g., 209) of the device, which contacts the vaginal wall and/or the ectocervix, can include one or more surface features such as ridges, contours, grooves, etc. The surface features may produce areas of concentrated pressure and that produce improved barriers to migration, relocation, proliferation, or movement of bacteria, bacterial byproducts, fungi, viruses or sperm. In some embodiments, the surface features act to guide bacteria, bacterial byproducts, fungi, viruses or sperm toward an introduced effect, or in a direction that makes migration, relocation, proliferation, or movement to a site adjacent to the cervix or in the cervical canal or uterus less likely.

Figure 3A:
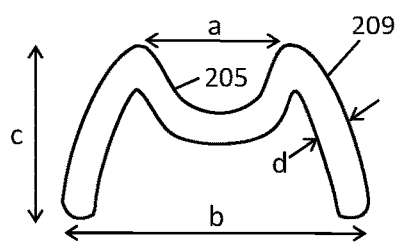
FIGS. 3A-3U illustrate section and perspective views of various example devices having features on an outer interface surface of the device to prevent material ascending from the vagina from passing between the device and the vaginal and/or cervical walls.

FIG. 3A shows a cross-section view (e.g., along a longitudinal cutting plane) of an example device in accordance with some embodiments. The dimensions of the device may vary depending on the size and/or shape of the ectocervix, as described herein. Referring to the example of FIG. 3A, typically, the diameter (a) (or width) of the dome region 205 ranges from about 25 millimeters (mm) to about 60 mm; the outer diameter (b) (width) of the device ranges from about 35 mm to about 75 mm; the height (c) of the device ranges from about 10 mm to about 35 mm; and a thickness (d) of at least a portion of the device (e.g., brim) ranges from about 1 mm to about 8 mm. As described herein, the outer interface surface 209 can be adapted to interface with the vaginal wall and/or the ectocervix surface. In some embodiments, the outer interface surface has a curved, convex shape.

Figure 3B:
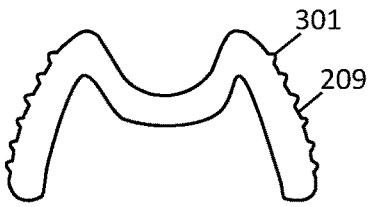
Figure 3C:
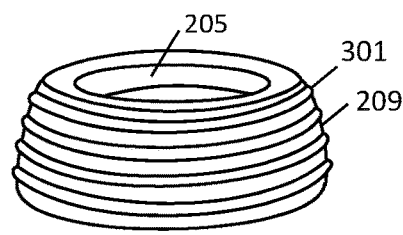
Figure 3D:
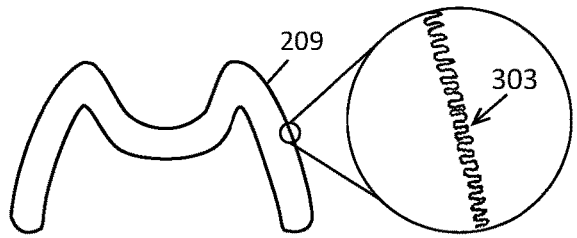
Figure 3E:
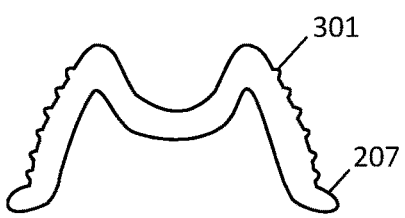

As described herein, in some embodiments, the outer interface surface (e.g., outer surface of the brim) includes one or more surface features to improve the prevention of movement of bacteria, bacterial by products, viruses, and/or sperm into the cervix and the uterus. FIGS. 3B-3E show example devices having various surface features. In each of the examples of FIGS. 3B-3E, the outer interface surface may be curved and have a convex shape (i.e., curved outward toward the vaginal wall and/or the ectocervix). FIG. 3B shows a cross-section view of a device having surface features 301 that protrude from the outer interface surface 209 of the device. The surface features 301 can be configured to concentrate force on the vaginal wall and/or the ectocervix at the surface features 301, which provides a barrier to prevent migration of sperm into the external os between the outer interface surface and one or both of the vaginal wall and the ectocervix. A shown in the perspective view of FIG. 3C, the surface features 301 may wind around the outer interface surface 209 to form one or more ring-shaped structures that wrap around the outer interface surface 209. In the example of FIG. 3C, the surface features 301 are substantially concentric to the opening defining the dome region 205. FIG. 3D shows a cross-section view of a different variation where the outer interface surface 209 has micropillars and/or nanopillars 303, which are very small surface protrusions that act mechanically as bactericides, thereby preventing such organisms from passing between the outer interface surface and the vaginal wall and/or the ectocervix wall. Such micropillars/nanopillars may also prevent migration of other organisms and cells, such as sperm, from passing between the outer interface surface and the vaginal wall and/or the ectocervix wall. FIG. 3E shows a cross-section view of different variation where the distal edge 207 of the device (also referred to as a base of the device) flares radially outward—in some cases, such that the outer diameter of the distal edge 207 is larger than other portions of the device.

Figure 3F:
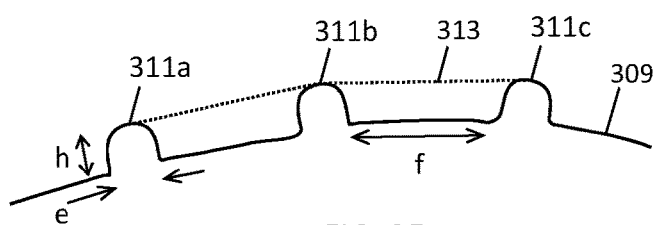

As described herein, the surface features on the outer interface surface can be configured to create a concentrated force on the vaginal wall and/or the ectocervix. A more concentrated force may be created when the surface features are on a convex outer interface surface compared to, for example, a flat surface. To illustrate, FIG. 3F shows a close-up cross-section view of a portion of a convex outer interface surface 309 having protruding surface features 311a, 311b and 311c. The dotted line 313 corresponding to the contour of the convex outer interface surface 309 illustrates that the surface feature 311b protrudes beyond the surface features 311a and 311c on either side due to the convex shaped surface from which they protrude. Thus, when the outer interface surface 309 is pressed on the vaginal wall/ectocervix, the tissue of the vaginal wall/ectocervix taut may interact with the surface feature 311b with a larger force than the surface features 311a and 311c, or if the surface feature was positioned on a flat surface.

The dimensions of the surface features may vary. In some variations, the surface features have the same height. In other variations, the surface features protrude at different height. In the example shown in FIG. 3F, the surface features 311a, 311b and 311c protrude by substantially the same height (h) from the curved interface surface 309. In some embodiments, the height of the surface features ranges from about 0.2 mm to 3 mm. In some embodiments, the distance (f) between the surface features ranges from about 0.2 mm to 8 mm. In some embodiments, the width (e) of the surface features ranges from about 0.2 mm to 4 mm.

Figure 3G:
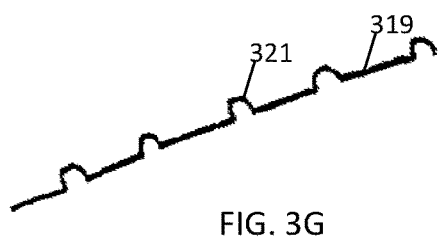
Figure 3H:
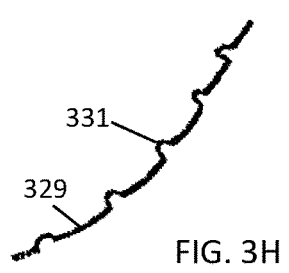
Figure 3I:
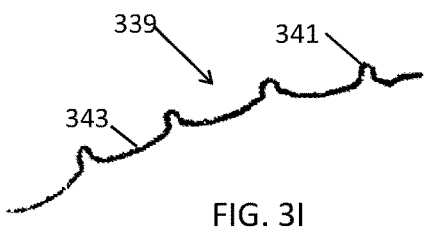

FIG. 3G shows a cross-section view of another variation where the surface features 321 protrude from a substantially flat outer interface surface 319. FIG. 3H shows a cross-section view of another variation where the surface features 331 protrude from a concave outer interface surface 329. FIG. 3I shows a cross-section view of another variation where the outer interface surface 339 has a generally convex shape, but where regions 343 between the surface features 341 are locally concave.

The surface features can have any of a number of shapes. FIGS. 3J-3P show cross-section views of various surface features having different shapes. FIG. 3J shows a curved shaped protruding feature; FIG. 3K shows a pointed (or triangular shaped) protruding feature; FIG. 3L shows a trapezoid shaped protruding feature; FIG. 3M shows a pointed angled protruding feature that points in a distal or proximal direction with respect to the cervix; FIG. 3N shows a heart shaped protruding feature; FIG. 3O shows an extended heart shaped protruding feature; and FIG. 3P shows features that extend from stem-like structures that provides some rotation of the features (constrained by the geometry) and that provide a "living hinge" aspect to the surface features. Each of the protruding features of examples of FIGS. 3J-3P can form one or more ring-shaped structures (similar to as shown in FIG. 3C) or one or more spiral/helical structures (similar to as shown in FIG. 3U) along the outer interface surface.

In some cases, the surface features form a surface pattern along the outer interface surface of the device. FIGS. 3Q-3T show aerial views of example surface patterns, with the shaded regions corresponding to protruding portions of the surface patterns. FIG. 3Q shows a protruding polygonal surface pattern; FIG. 3R shows a mesh surface pattern; FIG. 3S shows a surface pattern having indented holes; and FIG. 3T shows a surface pattern that forms ridges that may redirect ascending material (e.g., sperm and/or bacteria) or affect fluid resistance along the outer interface surface of the device.

In some embodiments, one or more generally helical structures (in some embodiments, with varying diameter) surround the ectocervix, to secure a desired position of the device and/or to maintain apposition between (a) a barrier to migration, relocation, proliferation, or movement of cellular organisms, microbes, bacteria, bacterial byproducts, viruses, fungi, spermatozoa, or their byproducts, and (b) cervical or vaginal tissue. In some embodiments, one or more ends of one or more of the generally helical structures terminates in a substantially closed circle. In some embodiments, the one or more generally helical structures allow the device to accommodate a range of ectocervical or vaginal morphologies. FIG. 3U shows a side view of another variation where a protruding surface feature 351 forms a helical (or spiral) shape around the outer interface surface 349. Such configuration may require the organism/sperm to travel multiple laps to reach either a channel exiting into a helix-bounded path 355. Optionally, a circumferentially complete ridge 353 is also included on a proximal end of the device (e.g., around the dome region, also referred to as a shoulder region) to provide a complete barrier.

In some embodiments, the device is configured to allow passage of egressing materials from the cervix, cervical canal, uterus, or a region bounded at least in part by the device and the vaginal wall or a portion of the cervix (for example, a region bounded in part by the endocervical canal), to a region bounded at least in part by the vaginal wall (for example, a region of the vagina anterior to the device). The device can allow passage of such material while still providing preventing cellular organisms, microbes, bacteria, viruses, fungi, spermatozoa, or their byproducts from entering into the cervix, cervical canal and/or uterus. For example, design features of the device can be used to guide cellular organisms, microbes, bacteria, viruses, fungi, spermatozoa, or their byproducts along one or more closed-ended paths, to enable later collection of the cellular organisms, microbes, bacteria, bacterial byproducts, viruses, fungi, spermatozoa, or their byproducts, or to prevent migration of the cellular organisms, microbes, bacteria, viruses, fungi, spermatozoa, or their byproducts to the cervix, cervical canal, or uterus. In some embodiments, the cellular organisms, microbes, bacteria, viruses, fungi, spermatozoa, or their byproducts to the cervix, cervical canal, or uterus are exposed to an introduced effect at one or more sites along the one or more closed-ended path, or at the end of the one or more closed-ended paths.

In some embodiments of the device, one or more paths (also referred to as channels) are provided that divert cellular organisms, microbes, bacteria, viruses, fungi, spermatozoa, or their byproducts to a location in the vagina, which might have otherwise migrated, relocated, proliferated, or moved to the cervix, cervical canal, or uterus. In some embodiments, the cellular organisms, microbes, bacteria, viruses, fungi, spermatozoa, or their byproducts to the cervix, cervical canal, or uterus are exposed to an introduced effect at one or more sites along the one or more paths, or at the end of the one or more paths.

Figure 4A:
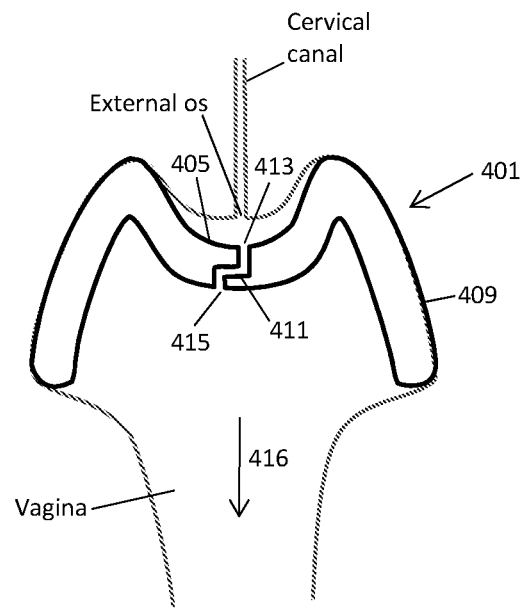
FIGS. 4A and 4B illustrate example devices having channels that allow material egressing from the cervix to travel through the channel toward the vagina while preventing material ascending the vagina towards the cervix from reaching the cervical canal.

FIG. 4A shows an example device 401 having a channel 411 (also referred to as a path) that allows passage of egressing materials (e.g., blood, mucus, etc. from the cervix, cervical canal, uterus, or a region bounded at least in part by the device and the vaginal wall or a portion of the cervix) from the external os in a distal direction 416 toward the lower vagina. In particular, the egressing material can travel into a first port 413 (also referred to as an opening or hole), through the channel 411 within a wall of the device, and out of the wall of the device through a second port 415. The channel can be within the wall of the dome region 405 that covers at least a portion of the ectocervix including the external os. Thus, the channel can pass through the thickness of the wall of the dome region 405 between a vaginal side of the dome region wall and a cervical side of the dome region wall. In some embodiments, the device includes multiple channels. The channel can be large enough to allow egressing material from the external os to travel through the channel and out the vaginal side of the dome region (e.g., by the force of gravity and/or movement of the body).

The channel can include at least portion 411 that runs non-parallel to the distal direction 416, which prevents material (e.g., cellular organisms, microbes, bacteria, viruses, fungi, spermatozoa) ascending from the vagina from reaching the external os. The non-parallel portion of the channel can create a longer path for the ascending material to travel, thereby reducing the probability that the ascending material will reach the external os. That is, any ascending material entering the second port 415 on the vaginal side will have to travel a longer distance within the channel due to the non-parallel portion compared to a completely straight channel (i.e., running parallel to distal direction 416); thereby reducing the chance that ascending material will exit the first port 413 on the cervical side.

Figure 4B:
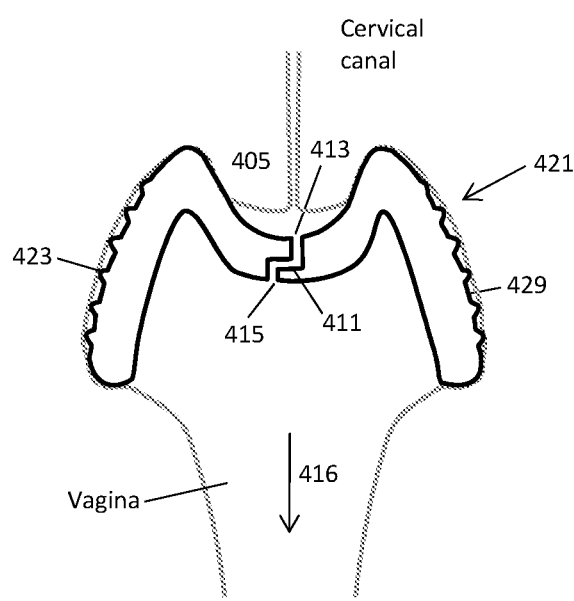

FIG. 4B shows another device 421 having similar features as the device 401, except that the outer interface surface 423 includes surface features 429 for improving the prevention of ascending material from reaching the external os around the outer interface surface 423, as described herein. Note that any of the devices described herein can include any of a number of combination of channels and surface features.

In general, the longer the channel travels in the non-parallel direction, the less the probability of the ascending material exiting the device (e.g., via the first port 413) and entering the external os. In some embodiments, the channel winds within the device to create a longer path for the ascending material to travel. In some embodiments, the device includes multiple channels and/or ports. In some embodiments, the channel(s) winds around at least a portion of a central axis of the device (e.g., of the dome region). In some embodiments, the channel(s) radiate from the central axis of the device (e.g., of the dome region).

FIGS. 5A-5L show aerial views (e.g., viewing the device from the top or from the bottom) showing various shapes that a channel may form with the device. A circle ("0") within the figures denote a second port (e.g., from the vaginal side of the dome region) or a first port (e.g., from the cervical side of the dome region). A line connecting the ports denote a channel within the wall of the device between the first and second ports (between the vaginal and cervical sides) of the dome region. The number of ports may be more than, less than, or equal to the number of channels in the device. FIG. 5A shows multiple channels that spiral around a central port; FIG. 5B shows a channel having a portions that extend radially from a central port to form a propeller like structure; FIG. 5C shows multiple channels that extend radially from a central port to form a flower-like structure; FIG. 5D shows multiple concentric channels each having an associated first and second port that are adjacent to each other and where the ports of each channel are radially offset with respect to one another; FIG. 5E shows a variation of FIG. 5D where the ports of each channel are aligned along a centerline; FIG. 5F shows a variation of FIG. 5E where the first ports of the channels are aligned along a first line and where the second ports of the channels are aligned along a second line; FIG. 5G shows two channels each having a sinuous path along one side of the device; FIG. 5H shows two channels each forming a maze-like path along one side of the device; FIG. 5I shows a single channel forming a maze-like structure within the device and having first and second ports at a central region of the device; FIG. 5J shows a variation of FIG. 5I where the first or second port is at a center of the device and the other of the first or second port is at a different location within the device; FIG. 5K shows a single channel that forms a sinuous path through the device where the first port is at one lateral side of the device and the second port is at an opposing lateral side of the device; and FIG. 5L shows multiple linear channels that radiate from a central port.

Figures 5M, 5N:
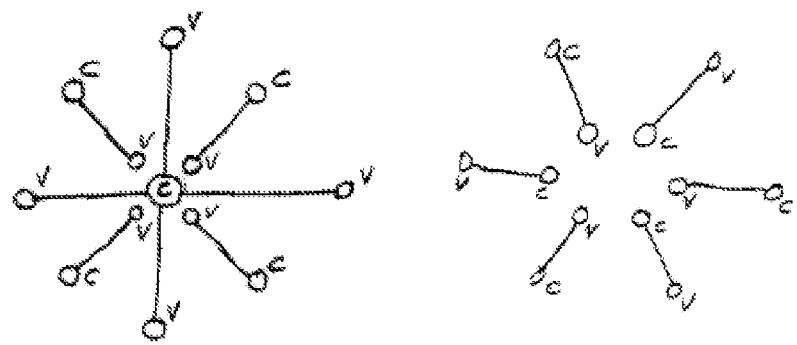

In some cases, the channel(s) may gain and/or lose elevation between the vaginal and cervical sides of the device. FIGS. 5M and 5N show aerial views of example channel shapes illustrating various elevation changes that the device may have. In FIGS. 5M and 5N, the ports labeled with a "V" denoted a port on the vaginal side of the device, and the ports labeled with a "C" denote a port on the cervical side of the device. As shown, different channels within the channel patterns in FIGS. 5M and 5N can gain or lose elevation. This may confuse the guidance mechanisms of the bacteria and/or sperm based on gravity and/or the temperature gradient within the body. This may also promote drainage of egressing material (e.g., fluid) from the cervix by ensuring that is at least one channel has a vaginal side exit that is lower in elevation than its cervical side entrance.

The channel(s) may be formed using any of a number of manufacturing techniques. For example, the channel(s) may be formed by etching the material of the device. In some cases, the channel(s) may be formed by laser drilling/cutting. In some cases, the channel(s) may be formed using a mold that includes a negative/positive region corresponding to the channel(s). In some cases, the device with the channel(s) formed therein may be formed using a three-dimensional (3D) printing process. In some cases, a combination of techniques is used (e.g., etching, laser drilling/cutting, molding and/or 3D printing).

The channel(s) may be formed within any portion of the device. In some variations, the channel(s) are within the dome region of the device that covers at least a portion of the ectocervix (e.g., FIG. 4A, 405). In some cases, the channel(s) are formed within a portion of the device that is manufactured separately than other portions of the device. For example, a dome region that includes the channel(s) may be formed using a first manufacturing process (e.g., including etching, laser drilling/cutting, molding and/or 3D printing) and a remainder of the device may be formed using a second manufacturing process. The dome region may then be integrated with the remainder of the device to form the full device. In other embodiments, the dome region with the channel(s) and a remainder of the device is formed in the same manufacturing process(es).

Figure 6:
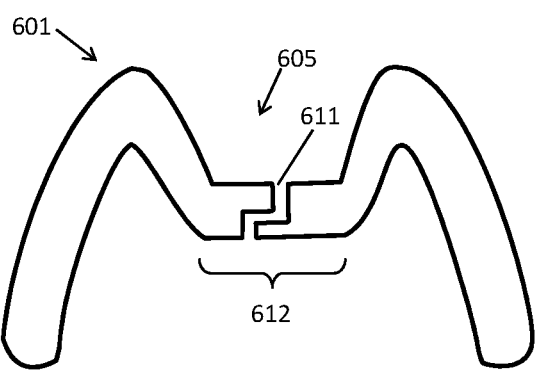
FIG. 6 illustrates another example device having a channel.

In some embodiments, at least a portion of the dome region has a substantially planar shape, as shown in the example device 601 of FIG. 6. In this example, the dome region 605 has a planar region 612 that includes the channel 611. This planar configuration may simplify the process for forming the channel within the device. In some cases, the planar region 612 may be manufactured separately, and then integrated into the remainder of the device, as described above.

Figure 7A:
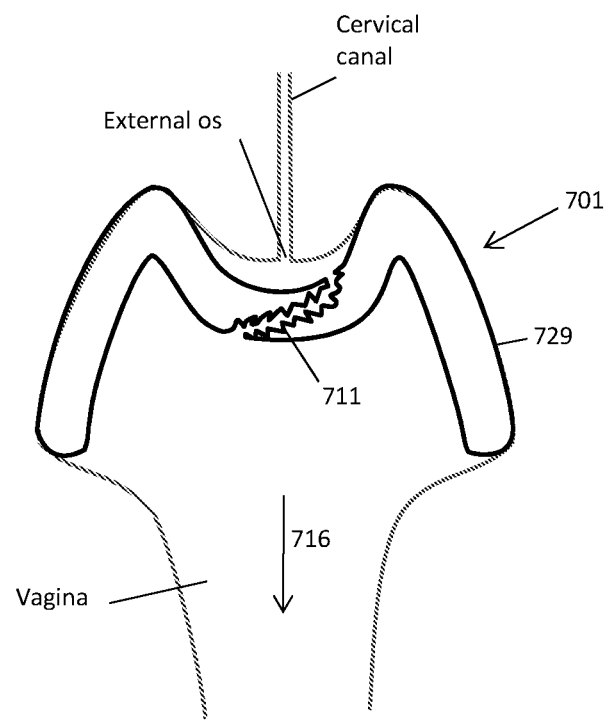
FIGS. 7A and 7B illustrate additional example devices having channels.

In some case, the internal walls of the channel includes one or more structures (e.g., microstructures) configured to impede movement of the ascending material, redirect the ascending material back toward the vagina and/or divert the ascending material within an area of the channel. FIG. 7A shows an example device 701, which includes a channel 711 having such a structure. The design of the structure along the internal walls of the channel can leverage aspects of the motility of certain type cells and organisms (e.g., sperm and bacteria) to control their movement. For example, sperm (and some bacteria) tend to swim along walls and concentrate (e.g., get stuck) along corners of a channel. Thus, the internal walls of the channel can be designed to guide and/or corral the sperm/bacteria such that they are directed away from the ectocervix. In some embodiments, at least a portion of the internal surface of the channel includes micropillars and/or nanopillars that have antimicrobial mechanical properties and configured to prevent migration microbial material and/or sperm to the cervical end of the channel. Note that at least a portion of the channel 711 runs in a non-parallel direction relative to the distal direction 716 (from the cervix toward the lower vagina). In some embodiments, the outer interface surface 729 has surface features (e.g., ridges) that provide a barrier from ascending material from passing between the device and the vaginal and/or cervical wall, as described herein.

Figure 7B:
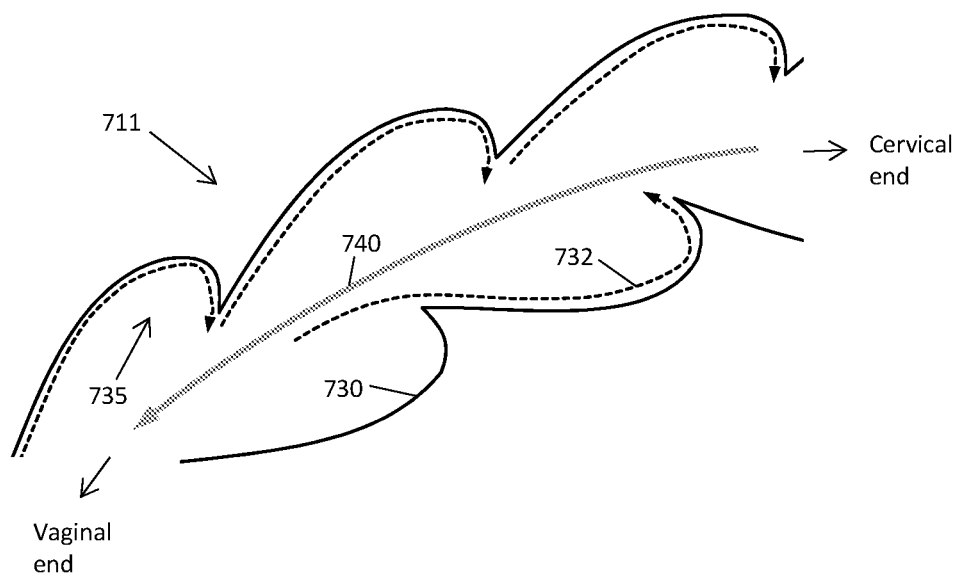

FIG. 7B shows a close up section view of an example channel 711 having internal walls 730 with a structure configured to control movement of ascending material. In the example of FIG. 7B, the internal walls 730 have redirecting features 735 that redirect ascending material (e.g., sperm, bacteria, etc.), denoted with dotted arrows 732, back toward the opening at the vaginal side of the dome. Meanwhile, egressing material (e.g., fluids) from the uterus and cervix is allowed to pass through a central region (referred to herein as a main channel path) of the channel, as denoted with the solid arrow 740 in FIG. 7B. Any of the redirecting features described herein can be arranged in series as a ratcheted arrangement, such as the example of FIG. 7B, which progressively directs the redirect ascending material (e.g., sperm, bacteria, etc.) away from the central path (e.g., 740). In the example of FIG. 7B, the redirecting features 735 correspond to curved lobes that are recessed (inset) with respect to the main channel path. In other examples, the redirecting features may have different shapes and/or may protrude partially into the main channel path. As used herein, a redirecting feature can refer to a structure that preferentially allow material (e.g., egressing fluid) to flow toward the vaginal end/side of the channel and/or that directs material (e.g., sperm and/or microbes) away from the cervical end/side of the channel. In sufficient numbers, the redirecting features placed in series along the fluid egress channel may reduce the probability of completed upstream migration to near zero.

The length of the channels described herein may vary depending on, for example, the diameter of the channel, the number of channels, the size of the device, etc. In some embodiments, the channel has a length of about 2 millimeters (mm) to 2500 mm. In some embodiments, the channel has a length of about 10 mm to 300 mm. The channels may have any diameter suitable for allowing egressing material to pass through to the vaginal side of the device and for sufficiently reducing the probability of ascending material of exiting the cervical side of the device. In some cases, the channel has a varied diameter (e.g., larger at the vaginal side, larger at the cervical side, or larger at an internal region between the vaginal and cervical sides). If the device includes multiple channels, the channels may have the same or different diameters. In some embodiments, the channel(s) passing through the device (not bounded in part by tissue) typically has/have a diameter of about 100 micrometers (μm) to 4 mm, and in some embodiments about 500 μm to 2.5 mm. In cases where the channel includes a structure, the diameter of the channel may vary along the path of the channel. Thus, the "diameter" of the channel having such structure features can be defined by a maximum distance between opposing sites along a length of the channel. In some embodiments, this maximum distance ("diameter") may range from about 100 micrometers to 4 mm (or from about 500 µm to 2.5 mm). The structures may typically range in size from about 50 micrometers to 1.5 mm (in some embodiments more from about 100 micrometers to 1 mm) in critical dimensions such as deviation from internal walls of the channel that follow the main channel path.

FIG. 7B shows one example structures effective for controlling movement of ascending material. However, other structure may also be effective in impeding, redirect and/or diverting the ascending material. In general, the size, shape and orientation of a redirecting feature (e.g., inset and/or protrusion) generally has a gradual curvature (or causes the cell/organism to travel along a gradual curvature path) to ensure a wall-tracking cell or organism (e.g., sperm or bacteria) is gradually redirected. If a redirecting feature along the channel wall curves away too abruptly (e.g., curves away with a radius of curvature <150 microns), the cell/organism may depart from the wall too quickly for effective redirecting. The tradeoff is that a gradual curvature may take up more channel length, which could otherwise be used for more redirecting structure features. In some embodiments, the transition into the redirecting feature (e.g., inset or protrusion) has a radius of curvature of about 150 micrometers or greater.

Figure 8A:
FIGS. 8A-8N illustrate section views of various additional example channels.
Figure 8B:
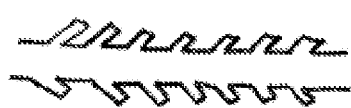
Figure 8C:
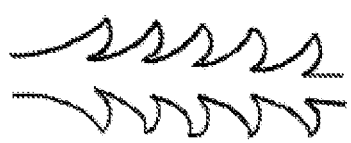
Figure 8D:
Figure 8E:
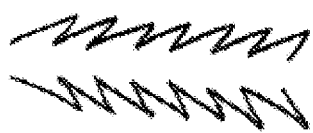
Figure 8F:
Figure 8G:
Figure 8H:
Figure 8I:
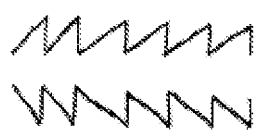
Figure 8J:
Figure 8K:
Figure 8L:
Figure 8M:
Figure 8N:
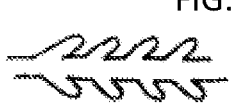

FIGS. 8A-8N shows close up section views of channels having internal wall with various redirecting features according to some embodiments. In each of the examples of FIGS. 8A-8N, the flow of ascending material is the same (as indicated in FIG. 8A, "cervical end" and "vaginal end"). FIG. 8A shows a channel having a series of curved lobes in a ratchet arrangement where the lobes on opposing walls are radially aligned with respect to one another. FIG. 8B shows a channel having a series of rectangular shaped insets in a ratchet arrangement where the rectangular features on opposing walls are radially aligned with respect to one another. FIG. 8C shows a channel having a series of curved features where opposing sides of the curved features are curved in the same direction. FIG. 8D shows a channel having a series of curled features that direct the cells/organisms to a holding region 801 that substantially traps the material therein. FIG. 8E shows a channel having a series of angled features in a ratchet arrangement where the angled features on opposing walls are radially aligned with respect to one another. FIG. 8E illustrates an angle of departure $\Theta$ (theta) for the cells/organisms relative to a channel direction in a curved lobe, showing that the angle of departure is generally reversed toward the vaginal end of the channel. FIG. 8G shows a channel having a series of cavities connected by a main channel path that enter and exits the cavities at laterally offset locations, which can cause the cells/organisms to collect at within the cavities. FIG. 8H shows a channel having a series of flaps that are arranged in a one-way valve configuration where fluid flow from the cervical end to the vaginal end causes the flaps to open but does not allow material to flow from the vaginal end to the cervical end. FIG. 8I shows a channel having a series of angled features similar to FIG. 8E, except that the angled features have larger angles. FIG. 8J shows a channel having a series of chevron shaped flaps that preferentially open with fluid flow from the cervical end to the vaginal end similar to FIG. 8H. FIG. 8K shows a channel having a series of lobes similar to FIG. 8A except the lobes on opposing walls are radially offset with respect to one another. FIG. 8L shows a close up view of the lobed structure of FIG. 8K illustrating how the departure angle for cells/organisms radially off the offset lobes can be asymmetric, thereby reducing collisions among the redirected cells/organisms and improving redirecting toward the vaginal end of the channel. FIG. 8M shows a channel having an intervening baffle within the main channel path that redirects the flow of egressing material around the baffle, which may provide more opposing flow resistance along the channel walls where the cells/organisms are concentrated, thereby reducing the chance of the cells/organisms reaching the cervical end of the channel. FIG. 8N shows a channel having a series of lobes having substantially straight channel wall segments between the lobes.

Figure 9A:
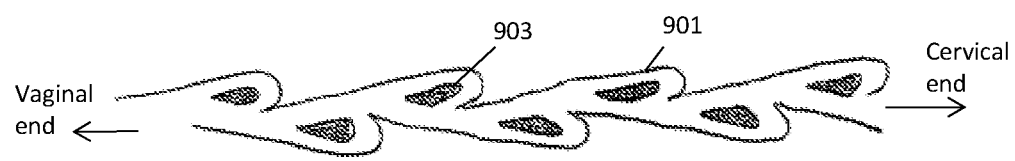
FIGS. 9A-9E illustrate section and perspective views of various additional example channels.

As described herein, optionally any of the variations described herein may include a channel with one or more valves that preferentially allow fluid to flow in one direction, including valves that open/close (e.g., closing the channel when flow is predominantly in one direction), as shown in FIG. 8H. More preferably, FIG. 9A shows a section view of a channel having an always-open valve arrangement. In the example of FIG. 9A, the channel include a valvular conduit (Tesla valve) arrangement with a series of curved lobes 903 and baffles 901 that provides a high resistance of flow toward the cervical end of the channel. Any of the apparatuses herein may be configured so that the channels are always open (e.g., not obstructed by a flap, etc.) even when increasing the resistance to flow in one direction.

It should be noted that although in some variations the open channels described herein may be configured to increase the resistance to flow in a first direction (e.g., from the vagina to the cervix) more than in the opposite direction (e.g., from the cervix to the vagina), these apparatuses may be configured to redirect sperm and/or motile microorganisms (bacteria, etc.) and viruses even without significantly increasing the resistance to flow in one direction relative to the other. This is because, as described herein, sperm and other motile organisms may preferentially travel along the wall(s) of the channel. Thus, if the channel walls direct the motile organism (e.g., sperm) generally in the first direction (e.g., from the cervix to the vagina), e.g., by providing curved or angled surfaces as shown and described above (e.g., in FIG. 7B), the motile organism may be redirected or steered back out of the channel from the vaginal side. This redirecting may occur even if the overall resistance to flow, which may be related to the width of the channel, for example, is nearly equivalent (e.g., less than 5-fold different, less than 4-fold different, less than 3-fold different, less than 2-fold different, etc.) in both directions. Thus, relatively large diameter channels may be used, preventing congestion of the channel(s) and allowing long-term usage (e.g., greater than 1 day, 2 days or longer, 3 days or longer, 5 days or longer, 1 week or longer, 2 weeks or longer, 3 weeks or longer, 4 weeks or longer, etc.) for any of the apparatuses described herein.

Figure 9B:
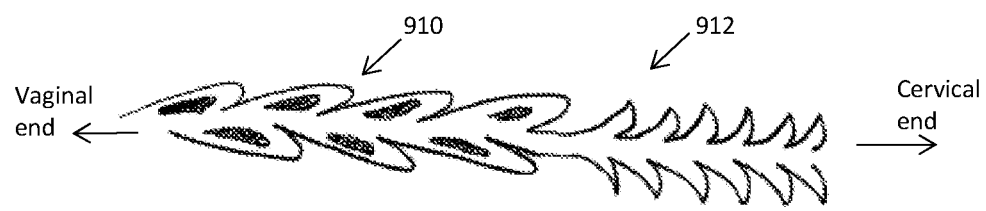

In some embodiments, the channels described herein have a first portion with first set of redirecting features and a second portion having a second set of redirecting features different from the first set of redirecting features. A channel may include any number of sets of different redirecting features. For example, a first set of redirecting features that preferentially allow fluid to flow in one direction (e.g., valves) may be strategically placed in a first portion of the channel, and a second set of redirecting features that prevents upstream movement of sperm and/or microbes may be strategically placed in a second portion of the channel. FIG. 9B shows such an example, where the channel has a first portion 910 with Tesla valves that preferentially allows fluid to flow toward the vaginal end of the channel, and a second portion 912 with curved recessed features that prevents upstream movement of sperm and/or microbes.

Figure 9C:
Figure 9D:
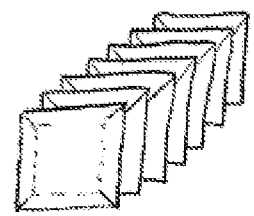

Any of the redirecting features described herein may be formed all the way around the channel or only partially around the channel. For example, the lobes in FIG. 8A may wind only partway around the circumference of the channel, which could form 3D heart structures in the channel. Alternatively, the lobes in FIG. 8A may wind all the way around the circumference of the channel forming a channel having a tiered lobe appearance. In some cases the features are radially symmetric around the circumference of the channel, while in other cases the features are not radially symmetric. For example, the aligned lobes in FIG. 8A may form a radially symmetric series of 3D lobes around the channel, while the offset lobes in FIG. 8K may form a radially unsymmetrical series of 3D lobes around the channel. FIGS. 9C and 9D show an example of a channel, with FIG. 9D illustrating a perspective view of the channel. As shown in FIG. 9D, the redirecting angled features in the channel wall can form pagoda-like structures in 3D.

Figure 9E:
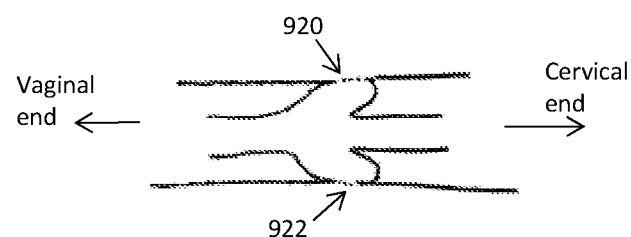

In some embodiments, the channels have one or more ports or semipermeable sections that allow fluid and/or air to pass into and/or out of the channel. FIG. 9E shows an example of a channel having sections 920 and 922 configured to allow fluid and/or air to pass into the lumen of the channel, which may "prime" the channel. In some cases, the sections 920 and 922 include one or more valve (e.g., one-way valves). In some cases, the sections 920 and 922 include a semipermeable barrier that allows fluid and/or air to pass through but not sperm/microbes.

Figure 10A:
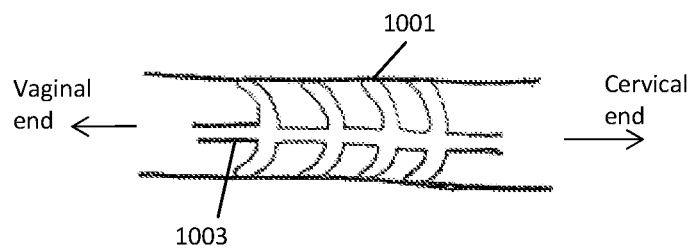
FIGS. 10A-10C illustrate section views of various additional example channels.
Figure 10B:
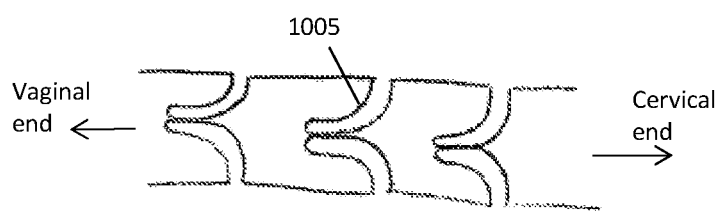
Figure 10C:
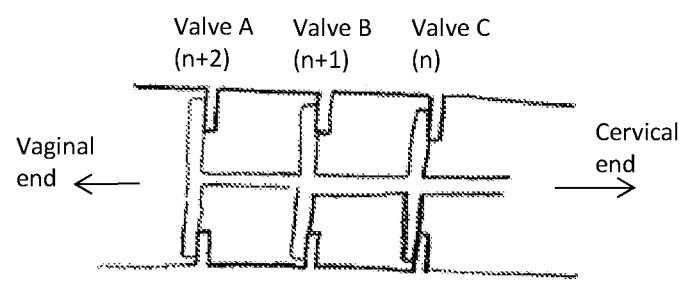

FIGS. 10A-10C show section views of example channels having various types of valves. In FIG. 10A, the channel includes a number of flaps 1001 attached to a central structure 1003 within the channel, where the flaps are configured to open by fluidic force applied in the direction toward the vaginal end of the channel and close by fluid force applied in the direction toward the cervical end of the channel, thereby acting as one-way valves. FIG. 10B shows another variation functioning similar to that of FIG. 10A except that the flaps 1005 are attached to the inner walls of the channel. FIG. 10C shows a variation where the pressure differential (pressure upstream vs. downstream) needed to open the valve flaps is lower for valves downstream verses the valve flaps upstream. For example, the pressure differential for opening valve A can be lower than that of valves B and C. Likewise, the pressure differential for opening valve B can be lower than that of valve C.

Figure 11A:
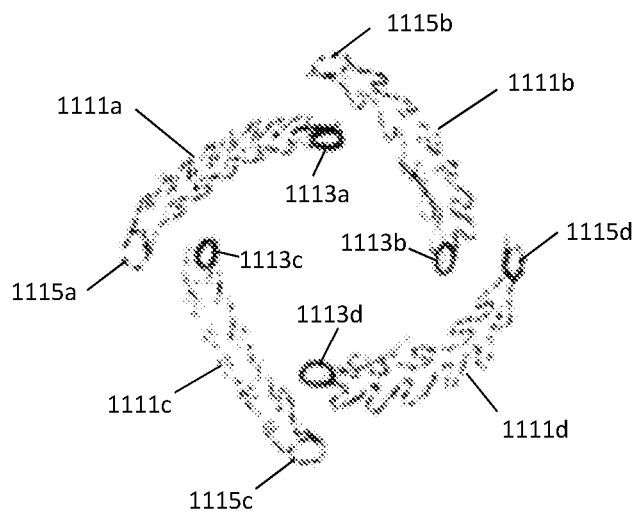
FIGS. 11A-11C illustrate various example channel paths.
Figure 11B:
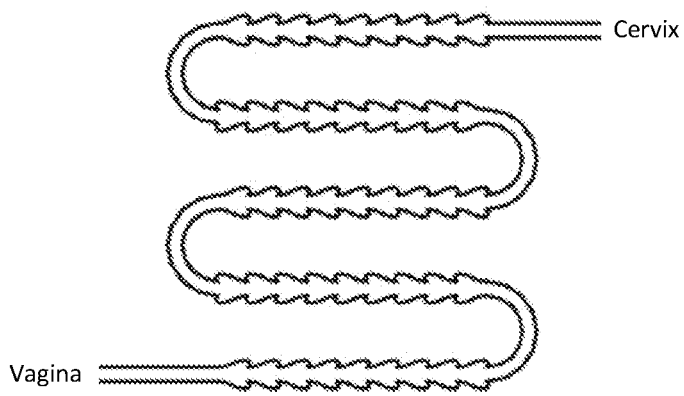
Figure 11C:
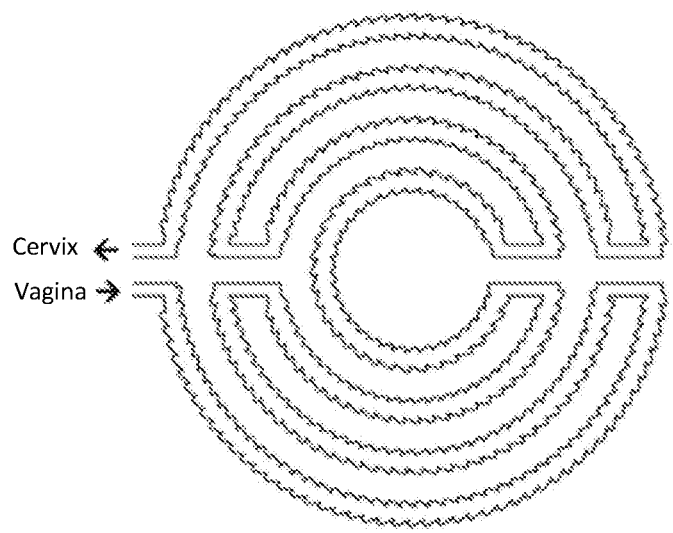

The channel(s) may be formed within any part of the device. In some cases, the channel(s) wind through the device in a continuous sinuous path, radiate from a central axis of the device, and/or zig zag across a width of the device, such as shown in various channel configurations in FIGS. 5A-5N. Any of the channel configurations described herein, including those described with reference to FIGS. 5A-5N, can include the structure (e.g., redirecting features) described herein. FIGS. 11A-11C show various other examples of channel configurations having structures. FIG. 11A shows an aerial view of a device that includes four channels (1111a, 1111b, 1111c and 1111d), each having a corresponding cervical end and vaginal end (1113a, 1113b, 1113c 1113d, 1115a, 1115b, 1115c and 1115d). Each of the channels includes a series of lobe-shaped redirecting features. As shown, the channels each form a curved shape around a central axis of the device. FIG. 11B shows a side view of a single channel that follows a serpentine path from the cervical side to the vaginal side of the device. FIG. 11C shows an aerial view of a single channel that forms a concentric maze-like path around a central axis of the device.

Figure 12A:
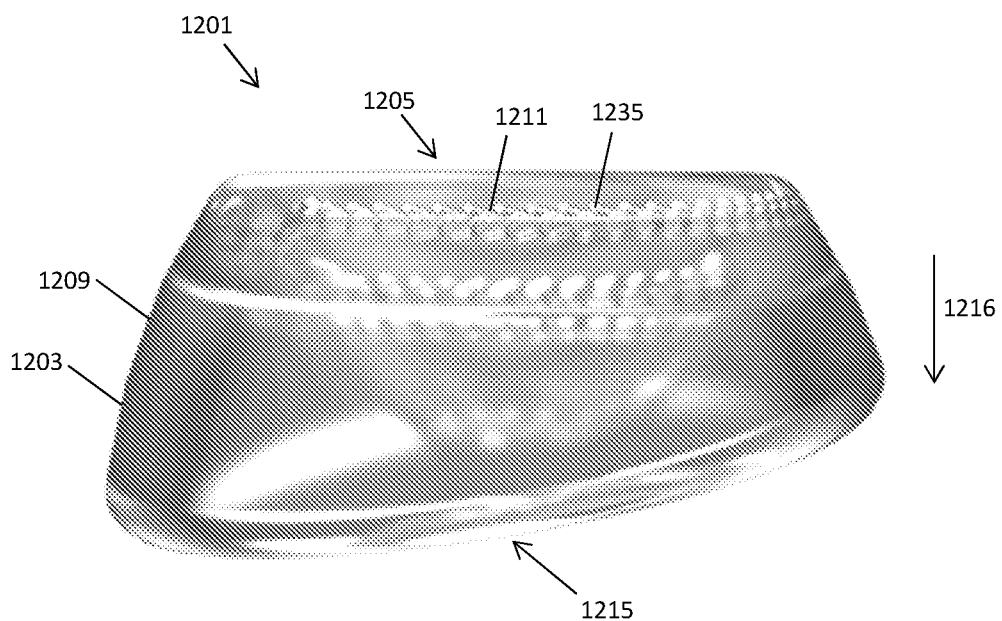
FIGS. 12A and 12B illustrate perspective views of an example device having a channel.
Figure 12B:
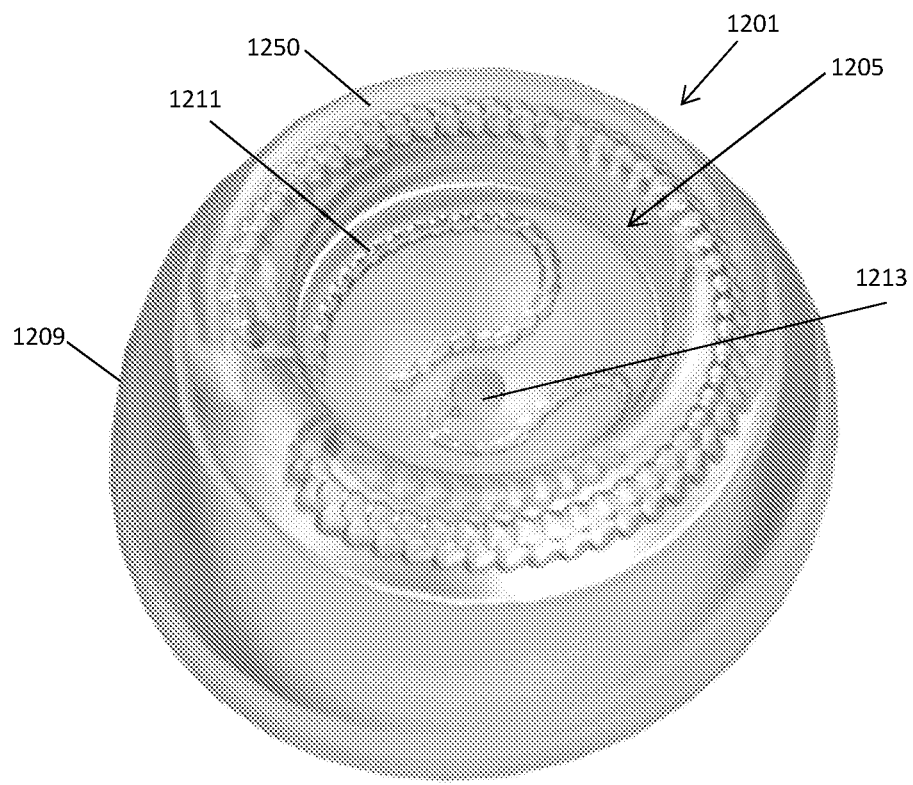

FIGS. 12A and 12B show perspective views of an example device 1201 showing a channel 1211 winding through portions of the device. A dome region 1205 of the device can be shaped and sized to fit over at least a portion of the ectocervix. The channel is configured to allow egressing material (e.g., fluid) from the external os entering a first port 1213 of the channel (e.g., on the cervical side of the dome region) to pass through the channel and out a second port 1215 of the channel (e.g., on the vaginal side of the dome region). A least a portion of the channel runs non-parallel to a distal direction 1216 toward the lower vagina. The channel includes series of redirecting features 1235 that are configured to direct the ascending material (e.g., sperm and/or microbes) back toward the lower vagina and/or direct the ascending material to a holding area of the channel. The surface of the dome region may be continuously connected to an outer interface surface 1209. The outer interface surface may be on a brim 1203 of the device. As shown, the channel may be embedded within the dome region and wind through the dome region and around the dome region, including within a shoulder region 1250 of the device corresponding to interface between the dome region and the outer interface surface. The outer interface surface, which can be configured to press against one or both of the vaginal wall and the ectocervix, may generally have a convex shape. In some embodiments, the outer interface surface includes one or more protruding features (e.g., arranged in one or more rings and/or helices) that are configured to concentrate force on one or both of the vaginal wall and the ectocervix at the one or more protruding features, thereby providing a barrier to migration of sperm into the external os between the outer interface surface and one or both of the vaginal wall and the ectocervix.

Figure 13A:
FIGS. 13A-13P illustrate close up section views of various example ports of channels.
Figure 13B:
Figure 13C:
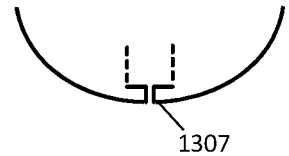
Figure 13D:
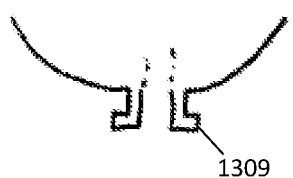
Figure 13E:
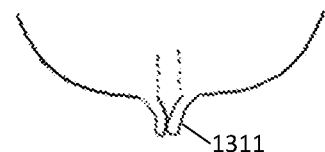
Figure 13F:
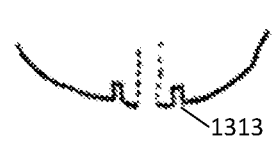
Figure 13G:
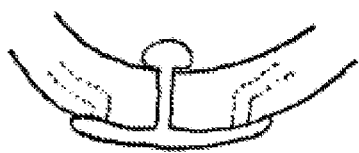
Figure 13H:
Figure 13I:
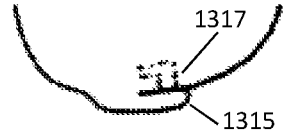
Figure 13J:
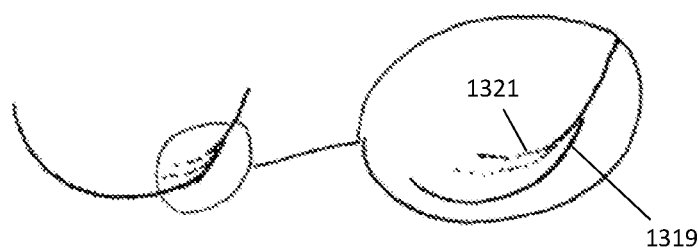
Figure 13K:
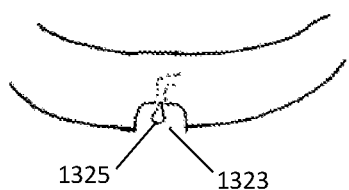
Figure 13L:
Figure 13M:
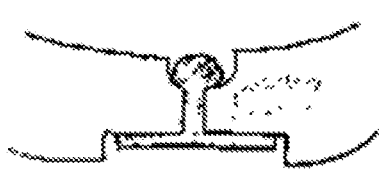
Figure 13N:
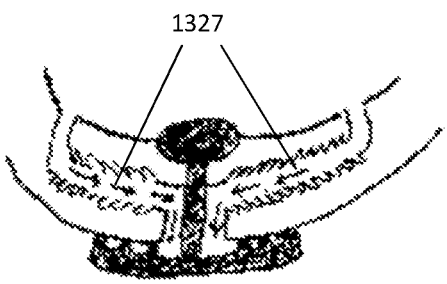
Figure 13O:
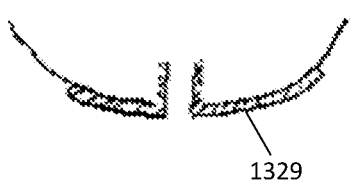
Figure 13P:

As described herein, any of the channels can include one or more redirecting features within the channel between the cervical end (e.g., first port) and the vaginal end (e.g., second port) of the channel. In some embodiments, such features are at the cervical end and/or at the vaginal end of the channel. FIGS. 13A-13P show close up section views of a number of example ports having redirecting features. In the examples shown in FIGS. 13A-13P, the convex surface (e.g., 1301) corresponds to an outer surface of the vaginal side of the dome region and the ports (e.g., 1303) correspond to the vaginal ends of the channels. The example of FIG. 13 shows a vaginal end port that is oriented in a non-parallel direction with respect to the distal direction of fluid flow from the cervix (e.g., on the side of the vaginal side of the dome region). This may arrangement can make it more difficult for material (e.g., microbes and/or sperm) to enter the port. FIG. 13B shows a variation similar to FIG. 13A and where the vaginal end port has a convex curvature. FIG. 13C shows a variation where the vaginal end port has a constricted section 1307, which can help to maintain a baseline fluid volume within the channel. FIG. 13D shows a variation including a standoff 1309 extending from the outer surface of the vaginal side and surrounding the vaginal end port, which can limit the amount of material (e.g., microbes and/or sperm) entering the port. FIG. 13E shows a valve 1311 configured to open upon fluid pressure out of the port and close upon fluid pressure into the port. FIG. 13F shows a variation including a recessed groove around the port, which can limit the amount of material (e.g., microbes and/or sperm) entering the port due to the tendency of sperm/microbes to congregate at corners/crevices. FIG. 13G shows a variation including an umbrella valve. FIG. 13H shows a variation including small ridges (e.g., micropillars or nanopillars) around the port, which can limit the amount of material (e.g., microbes and/or sperm) entering the port. FIG. 13I shows a variation including a flap valve 1315 and an "L" shaped port 1317. FIG. 13J shows a variation including flap valve 1319 and a curved port 1321 so that pressure in the channel pushes the flap aside for fluid to exit. FIG. 13K shows a variation including a recess 1323 around the port, where the depth of the recess is large enough to exceed the drop size 1325 of fluid exiting the port so that a fluid bridge is less likely to form. The recess 1323 can also prevent the port from contacting body tissue. FIG. 13L shows a variation including a slit valve, which can be opened by pressure from egressing materials or by squeezing. FIGS. 13M and 13N shows different variations of umbrella valves. In FIG. 13N, the umbrella valve is configured to concentrate fluidic force around the valve in a direction 1327 toward the port. FIG. 13O shows a variation including a hydrophobic coating 1329, such as a surface finish or material, which causes fluid to flow away from the port. The hydrophobic coating may also act as a microbicide and/or spermicide. FIG. 13P shows a variation including a duckbill valve (or slit valve) that is recessed from the outer surface of the vaginal side of the dome region to prevent unwanted interaction with body tissue of the wearer or partner.

As described herein, the channels can prevent ascension of materials such as organisms, cells, and their byproducts into the cervical canal while allowing fluids from the uterus and/or cervical canal to egress toward the lower vagina and eventually out of the body. This may allow the device to be worn of a longer period compared to other cervical cap devices. For example, in some cases, the devices described herein may be worn on the ectocervix for at least 24 hours. In some cases, the devices described herein may be worn on the ectocervix for 48 hours or more. In some cases, the devices described herein may be worn on the ectocervix for more than 48 hours (e.g., at least 49 hours, at least 50 hours, at least 72 hours, etc.). In some cases, the devices can be worn during sexual intercourse.

As described herein, any of the devices may be used with light (e.g., blue light) as an antimicrobial and/or a spermicide. For example, the material of at least a portion of the device having the channel(s) embedded therein may be at least partially transparent to the applied light so that when the light is shone on the device, the light reaches any microbes and/or sperm within the channel effective for killing the microbes and/or sperm. That is, the material of the device may be sufficiently transparent to allow the light to shine through a thickness of the material to reach the lumen of the channel(s) embedded within the device. In some examples, the device includes one or more light sources (e.g., light-emitting diode(s)) on or within the device. Thus, the microbes and/or sperm within the channel may be killed by activating (e.g., turning on) the light source(s).

In some embodiments, one or more surfaces of the device includes an anti-microbial texture or biofilm that is non-hospitable to bacterial and/or sperm. For example, the outer interface surface can include a surface textures and/or film that makes it hard for bacteria and/or sperm to wiggle along the device-tissue interface. In some cases, one or more channels of the device includes such a textured surface and/or biofilm.

In some embodiments, the device may be used with medicament (e.g., gel, cream or liquid), such as a bactericide, spermicide, fungicide, and/or antiviral medication. In some embodiments, the devices may be effective used to prevent pregnancy and/or infection without such additional medicine.

In some embodiments, multiple features or introduced effects are employed to prevent migration, relocation, proliferation, or movement of cellular organisms, microbes, bacteria, viruses, fungi, spermatozoa, or their byproducts to the cervix, cervical canal, or uterus, which may improve overall device effectiveness, or may prevent bacterial resistance to one or more introduced effects from occurring. In some embodiments, these multiple features or introduced effects are employed in series along at least one path of potential migration, relocation, proliferation, or movement.

In some embodiments, the device is configured to trap or collect some or all of the egressing material. In some embodiments, an antimicrobial, antibacterial, bacteriostatic, antiviral, antifungal, or spermicidal effect (for example, an introduced effect, as previously defined) is provided; in some embodiments, the effect is provided in a first region or in a manner that isolates cellular organisms, microbes, bacteria, viruses, fungi, spermatozoa, or their byproducts in a second region from the effect, in order, for example, to avoiding changing or minimize a change to the vaginal microbiome.

In some embodiments of the device, cellular organisms, microbes, bacteria, viruses, fungi, spermatozoa, or their byproducts are prevented from reaching a site in or at the cervix, cervical canal, or uterus, said prevention achieved without altering or significantly altering the vaginal microbiome; in some examples, this is achieved by isolating the vaginal microbiome from an introduced effect delivered to cellular organisms, microbes, bacteria, viruses, fungi, spermatozoa, or their byproducts that reach a site on or within the device while migrating toward the cervix, cervical canal, or uterus.

In some embodiments of the device, introduced effects are delivered at or within a region that prevents exposure of at least a portion of vaginal tissue, cervical tissue, cervical mucus, the cervical mucus plug, amniotic tissue, or uterine tissue to the introduced effect.

In some embodiments of the device, a shielding feature or configuration prevents a harmful wavelength, intensity, duration, or dosage of light from reaching at least a portion of vaginal tissue, cervical tissue, cervical mucus, the cervical mucus plug, amniotic tissue, or uterine tissue.

In some embodiments of the device, a filter, or the filtering property of a constituent material of the device, prevents a harmful wavelength, intensity, duration, or dosage of light from reaching at least a portion of vaginal tissue, cervical tissue, cervical mucus, the cervical mucus plug, amniotic tissue, or uterine tissue.

In some embodiments, the device features a path of passage for egressing materials from a first site in the cervical canal through and/or around the device to a second site in the vagina that is longer, and in some embodiments much longer, than the path from the first site to the second site would be without the device. A long path of passage could serve several functions, including but not limited to the following: (a) creating a long path for cellular organisms, microbes, bacteria, viruses, fungi, spermatozoa, or their byproducts to migrate, relocate, proliferate, or move from the vagina toward the cervix, cervical canal, or uterus, which may make migration, relocation, proliferation, or movement to the cervix, cervical canal, or uterus via that path less likely; (b) exposing the cellular organisms, microbes, bacteria, viruses, fungi, spermatozoa, or their byproducts migrating, relocating, proliferating, or moving from the vagina toward the cervix, cervical canal, or uterus via that path to introduced effects, in some embodiments for a greater duration, or distance, or at a greater intensity, than might occur with a shorter path; (c) facilitating exposure (or a degree, duration, or intensity of exposure) of cellular organisms, microbes, bacteria, viruses, fungi, spermatozoa, or their byproducts migrating, relocating, proliferating, or moving from the vagina toward the cervix, cervical canal, or uterus to introduced effects while preventing, minimizing, or eliminating exposure (or a degree, duration, or intensity of exposure) of tissue or other bacteria (for example, other bacteria comprising the microbiome of the reproductive system) to introduced effects, for example by routing the path through a region from which tissue or other bacteria (for example, other bacteria comprising the microbiome of the reproductive system) are shielded. In some embodiments, the degree, duration, or intensity of exposure facilitated causes bacteria, bacterial byproducts, viruses, or sperm to be killed or destroyed. In some embodiments, a path of passage is at least partly coated or lined with a hydrophobic material, such as PTFE, which may reduce fluid resistance.

In some embodiments, no introduced effect is delivered to a primary path of passage of egressing materials, while an introduced effect is delivered to another path configured to intercept, attract, or trap cellular organisms, microbes, bacteria, viruses, fungi, spermatozoa, or their byproducts migrating on, over, or through the device.

In some embodiments, the device has a feature used to aid in the delivery of a substance to sites on or within the device. For example, the device may have one or more entrance ports through which a bacteriostatic, antimicrobial, antiviral, antifungal, or spermicidal substance, or a substance which prevents migration of cellular organisms, microbes, bacteria, bacterial byproducts, viruses, fungi, spermatozoa, or their byproducts, may be introduced to a desired site within or on the device. In some embodiments, the device may have one or more exit ports from which the substance exits the device, to which a hose, a tube-like feature, or a syringe may be connected. In some embodiments, entrance and exit ports function, along with components connected thereto, to enable delivery of the substance, evacuation of air, or collection of preceding contents on or within the sites. In some embodiments, delivery of the substance is performed while the device is worn; in some embodiments, delivery of the substance is performed before the device is worn. In some embodiments, removal of contents is performed while the device is worn; in some embodiments, removal of contents is performed after the device is removed. In some embodiments, the substance attracts or repels cellular organisms, microbes, bacteria, viruses, fungi, spermatozoa, or their byproducts in a desired direction.

In some embodiments of the device, in which an antibacterial, antiviral, anti-fungal, antimicrobial, bacteriostatic, or spermicidal agent is used to damage, compromise, neutralize, or kill cellular organisms, microbes, bacteria, bacterial byproducts, viruses, fungi, spermatozoa, or their byproducts, a feature such as a one-way valve is positioned to prevent the agent from moving from a first site within or on the device to a second site, for example a second site adjacent to the cervix, within the cervical canal, within the uterus, or within the vagina. In some embodiments, the feature such as a one-way valve is positioned along a path of passage of egressing materials.

In some embodiments, a surface over which, or a passage through which, cellular organisms, microbes, bacteria, viruses, fungi, spermatozoa, or their byproducts may migrate, relocate, proliferate, or move is coated with, has contact with, or is comprised of an antimicrobial, antiviral, antifungal, bacteriostatic, or spermicidal agent. In some embodiments, exposure to the agent is limited to or concentrated on cellular organisms, microbes, bacteria, viruses, fungi, spermatozoa, or their byproducts that have migrated, relocated, proliferated, or moved toward the cervix or the uterus from a site in the vagina.

In some embodiments, a path of potential migration, relocation, proliferation, or movement of cellular organisms, microbes, bacteria, viruses, fungi, spermatozoa, or their byproducts is coated with, has contact with, or is comprised of two or more anti-microbial, antiviral, antifungal, bacteriostatic, or spermicidal agents, such that cellular organisms, microbes, bacteria, viruses, fungi, spermatozoa, or their byproducts that may not be killed, compromised, or damaged by one agent may be killed, compromised, or damaged by another, and such that a single device may provide protection against multiple potential infections, or against a pregnancy and one or more potential infections.

Embodiments which utilize one or more antimicrobial, antiviral, anti-fungal, bacteriostatic, or spermicidal agents may utilized one or more of a variety of agents, including but not limited to: silver, silver ion, silver alloy, copper, copper ion, copper alloy, zinc, zinc alloy, chlorhexidine, chlorhexidine gluconate, iodine, povidone-iodine, octenidine dihydrochloride, polyhexanide, sodium hypochlorite, sodium bicarbonate, hydrogen peroxide, protease inhibitors, lactic acid, citric acid, acetic acid, essential oils, nonoxynol-9, sodium docecyl sulfate, C31G, BufferGel, polyanions, carrageenans, cellulose sulfate, VivaGel, antiretroviral agents, tenofovir, dapivirine, UC-781.

In some embodiments, a bacteriostatic, antimicrobial, antiviral, or spermicidal substance is positioned to contact cellular organisms, microbes, bacteria, viruses, fungi, spermatozoa, or their byproducts that are migrating from a first site on or within the cervix, within the cervical canal, or in the uterus to a second site in the vagina, without contacting tissues that are contacted by the device.

In some embodiments of the device, a substance to which cellular organisms, microbes, bacteria, viruses, fungi, spermatozoa, or their byproducts are attracted is used to guide cellular organisms, microbes, bacteria, viruses, fungi, spermatozoa, or their byproducts in a direction or toward a destination that will make migration, relocation, proliferation, or movement of the cellular organisms, microbes, bacteria, viruses, fungi, spermatozoa, or their byproducts to the cervix, cervical canal, or uterus less likely. In some instances, the attracting substance may attract cellular organisms, microbes, bacteria, viruses, fungi, spermatozoa, or their byproducts toward a region of the vagina. In some instances, the attracting substance may attract bacteria, bacterial byproducts, viruses, or sperm toward an introduced effect. In some instances, the attracting substance may attract cellular organisms, microbes, bacteria, viruses, fungi, spermatozoa, or their byproducts to a collection site within the device. In some instances, a gradient or variation of the attracting substance is provided along a path of migration, relocation, proliferation, or movement.

In some embodiments of the device, a substance from which cellular organisms, microbes, bacteria, viruses, fungi, spermatozoa, or their byproducts are repelled is used to guide cellular organisms, microbes, bacteria, viruses, fungi, spermatozoa, or their byproducts in a direction or toward a destination that will make migration, relocation, proliferation, or movement of the cellular organisms, microbes, bacteria, viruses, fungi, spermatozoa, or their byproducts to the cervix, cervical canal, or uterus less likely. In some instances, the repelling substance may guide cellular organisms, microbes, bacteria, viruses, fungi, spermatozoa, or their byproducts toward a region of the vagina. In some instances, the repelling substance may guide cellular organisms, microbes, bacteria, viruses, fungi, spermatozoa, or their byproducts toward an introduced effect. In some instances, the repelling substance may guide cellular organisms, microbes, bacteria, viruses, fungi, spermatozoa, or their byproducts to a collection site within the device. In some instances, a gradient or variation of the repelling substance is provided along a path of migration, relocation, proliferation, or movement.

In some embodiments of the device, rigidity, density, porosity, roughness, smoothness, topography, temperature, or adhesiveness, or gradients or variations thereof, of the material or surface over which, to which, or through which cellular organisms, microbes, bacteria, bacterial byproducts, viruses, fungi, spermatozoa, or their byproducts, relocate, proliferate, or move are used to guide bacteria, bacterial byproducts, viruses, or sperm in a direction or toward a destination that will make migration, relocation, proliferation, or movement to the cervix, cervical canal, or uterus less likely. In some instances, rigidity, density, porosity, roughness, smoothness, topography, temperature, or adhesiveness, or gradients or variations thereof, of the material or surface over which or through which cellular organisms, microbes, bacteria, viruses, fungi, spermatozoa, or their byproducts migrate, relocate, proliferate, or move may guide bacteria, bacterial byproducts, viruses, or sperm toward a region of the vagina. In some instances, rigidity, density, porosity, roughness, smoothness, topography, temperature, or adhesiveness, or gradients or variations thereof, of the material or surface over which or through which cellular organisms, microbes, bacteria, viruses, fungi, spermatozoa, or their byproducts migrate, relocate, proliferate, or move may guide cellular organisms, microbes, bacteria, viruses, fungi, spermatozoa, or their byproducts toward an introduced effect. In some instances, rigidity, density, porosity, roughness, smoothness, topography, temperature, or adhesiveness, or gradients or variations thereof, of the material or surface over which or through which cellular organisms, microbes, bacteria, viruses, fungi, spermatozoa, or their byproducts migrate, relocate, proliferate, or move may cellular organisms, microbes, bacteria, viruses, fungi, spermatozoa, or their byproducts to a collection site within the device. In some instances, principles of plithotaxis, durotaxis, haptotaxis, or mechanotaxis are leveraged to achieve a desired migration, relocation, proliferation, or movement of bacteria, bacterial byproducts, viruses, or sperm.

In some embodiments of the device, nano-structures, micro-structures, protrusions, or other topographical elements on a surface of the device are configured to damage, or guide in a desired direction, cellular organisms, microbes, bacteria, bacterial byproducts, viruses, fungi, spermatozoa, or their byproducts. In some embodiments, these structures mimic surfaces, or the effects of surfaces, found on insects (including the cicada, butterfly, and dragonfly), gecko feet, or the leaves of lotus, taro, or other plants. In some embodiments, these nano-structures, micro-structures, protrusions, or other topographical elements puncture, distend, stretch, rupture, or otherwise adversely affect cell walls, making migration, relocation, proliferation, or movement to a cervix, cervical canal, or uterus less likely. These nano-structures, structures, protrusions, or other topographical elements may be a variety of shapes, including but not limited to barb-shaped, bulged, hair-like, ribbed, scale-like, cylindrical, conical, or generally pointed shapes. They may emerge at a variety of angles to a general surface from which they emerge, including angles of exactly or nearly 90 degrees, angles nearly parallel to the general surface such as 3 degrees, or angles in between 3 and 90 degrees. They may assume a variety of heights from the general surface from which they emerge, including heights between 100 nanometers and 75 microns. In some instances, these nano-structures, micro-structures, protrusions, or other topographical elements are incorporated into the device by heat-forming a surface of the device, plastically deforming a surface of the device, or applying a structure featuring these nano-structures, micro-structures, protrusions, or other topographical elements to a surface of the device.

In some embodiments, light is used to attract cellular organisms, microbes, bacteria, viruses, fungi, spermatozoa, or their byproducts toward an introduced effect.

In some embodiments, a path of lesser resistance to migration, relocation, proliferation, or movement is made available to cellular organisms, microbes, bacteria, viruses, fungi, spermatozoa, or their byproducts or egressing material, leading toward a destination (for example, the lower vagina or a site of collection) to which migration, relocation, proliferation, or movement is desired.

In some embodiments, an adhesive surface acts to trap cellular organisms, microbes, bacteria, viruses, fungi, spermatozoa, or their byproducts that might otherwise migrate, relocate, proliferate, or move over the surface toward the cervix, cervical canal, or uterus. In some embodiments, the adhesive surface is located such as to avoid contact with vaginal, cervical, or uterine tissue or a cervical mucus plug.

In some embodiments, devices have a surface coating or topography that guides or attracts migrating, relocating, or proliferating cellular organisms, microbes, bacteria, viruses, fungi, spermatozoa, or their byproducts away from a path that travels toward the uterus. In some embodiments, the surface coating or topography is more favorable or attractive to migrating bacteria than a path toward the uterus between the device and ectocervical or vaginal tissue. In some embodiments, a surface roughness on a path that leads to a containment region in the device or toward the lower vagina is more conducive to migration, relocation, or proliferation of cellular organisms, microbes, bacteria, viruses, fungi, spermatozoa, or their byproducts than a path (for example, a path between the device and the ectocervical or vaginal tissue) that leads toward the uterus (such as some paths between the device and the ectocervical or vaginal tissue). In some embodiments, the surface coating or topography provides conditions that are chemotaxic to the cellular organisms, microbes, bacteria, bacterial byproducts, viruses, fungi, spermatozoa, or their byproducts. In some embodiments, a heat source within the device attracts cellular organisms, microbes, bacteria, bacterial byproducts, viruses, fungi, spermatozoa, or their byproducts.

In some embodiments of the device, light (such as ultraviolet light or blue light) is used to damage or kill cellular organisms, microbes, bacteria, bacterial byproducts, viruses, fungi, spermatozoa, or their byproducts. In some embodiments of the device, the light is delivered by a light-emitting diode on or within the device. In some embodiments of the device, the light is delivered to a potential path of migration, relocation, proliferation, or movement between the device and tissue, for example between the device and the vaginal wall, or between the device and the cervical surface. In some embodiments of the device, the light is delivered to a surface of the device that does not contact tissue. In some embodiments of the device, the light is delivered to at least a portion of a path of potential migration that provides a path of passage for egressing materials from the cervix, cervical canal, or uterus. In some embodiments of the device, the light is shielded to prevent tissue, for example vaginal or cervical tissue, from being exposed to the light, or from being exposed to a wavelength, intensity, or duration of light. In some instances, design features of the device are selected to increase the likelihood that cellular organisms, microbes, bacteria, viruses, fungi, spermatozoa, or their byproducts that might migrate, relocate, proliferate, or move to the cervix, cervical canal, or uterus follow a path that increases the likelihood, duration, or intensity of exposure to the light (or another introduced effect). For example, the migration, relocation, proliferation, or movement path through or on the device may wind, reverse in direction, curve, or circumnavigate on or within the device, or may include a region with a volume that slows the migration, relocation, proliferation, or movement speed, for example acting as a reservoir, prolonging the duration of exposure to the light or other introduced effect delivered in the region. In some embodiments, a path of potential migration, relocation, proliferation, or movement of cellular organisms, microbes, bacteria, viruses, fungi, spermatozoa, or their byproducts is configured such that the distance that light (such as ultraviolet light or blue light) must pass through egressing material to reach cellular organisms, microbes, bacteria, viruses, fungi, spermatozoa, or their byproducts in the egressing material is sufficiently short to ensure that a lethal, damaging, or compromising intensity, duration, wavelength, or dosage of light is delivered.

In some embodiments, a wavelength of light is provided that is spermicidal (for example, 265 nm). In some embodiments, a wavelength of light is provided that is microbicidal (for example, 400-500 nm). In some embodiments, an intensity, duration, and wavelength of light are chosen to avoid enhancing proliferation of microbes. In some embodiments, an intensity, duration, and wavelength of light are chosen in order to kill a minimum percentage of microbes exposed to the light (for example 99.9%).

In some embodiments, the device uses a wavelength, duration of exposure, or intensity of light that has a lethal effect on targeted microbes, bacteria, fungi, or viruses, but is not harmful or minimally harmful to human tissues exposed to the light. In some embodiments, the light has a far-UVC wavelength. In some embodiments, the device uses blue light that is not in the UV spectrum.

In some embodiments of the device, light is turned on or off in order to ensure an antimicrobial, antiviral, antibacterial, antifungal, or spermicidal effect is achieved, or to preserve battery life. The light may be turned on or off according to or for reasons including but not limited to one or more of the following: a programmed schedule, including a schedule that ensures that the light is not off for a length of time exceeding a specific duration; the opening of a valve; the arrival or accumulation of egressing material at a site on or within the device.

In some embodiments, the device has multiple lights in order to provide different wavelengths, intensities, or durations of light exposure along a path of potential migration of cellular organisms, microbes, bacteria, bacterial byproducts, viruses, fungi, spermatozoa, or their byproducts. In some embodiments, the multiple lights function to provide introduced effects that are optimized for different targets.

In some embodiments, materials resistant to damage from ultraviolet or blue light are used for constituents of the device exposed to ultraviolet or blue light.

In some embodiments, one or more lights providing a bacteriostatic, microbicidal, antiviral, antifungal, or spermicidal effect or an indication of a status may be switched on or off. In some embodiments, the one or more lights are switched on prior to delivery of the device to a site at, adjacent to, or over a portion of a cervix.

In some embodiments, electroluminescent wires, panels, ribbons, coatings, or other structures are used to deliver light that kills, attracts, or repels cellular organisms, microbes, bacteria, viruses, fungi, or spermatozoa. In some embodiments, one or more electroluminescent structures partly or fully surround or line a path of potential migration of cellular organisms, microbes, bacteria, viruses, fungi, or spermatozoa. In some embodiments, an electroluminescent structure is placed within a channel, and/or defines a channel, through which egressing materials pass and through which cellular organisms, microbes, bacteria, viruses, fungi, or spermatozoa could migrate. In some embodiments, an electroluminescent structure provides light through a translucent structure onto a path by which cellular organisms, microbes, bacteria, viruses, fungi, or spermatozoa could migrate to a site within a cervix or uterus. In some embodiments, the electroluminescent structures are electrically coupled to an inverter and a battery contained within the device.

In some embodiments, at least a portion of the device is comprised of protecting material that protects tissue near the device from harmful wavelengths or dosages of light. In some embodiments, the protecting materials is translucent to safe wavelengths or dosages of light.

In some embodiments, a filter material allows egress of egressing material from the cervix, cervical canal, or uterus through the device, but traps cellular organisms, microbes, bacteria, viruses, fungi, spermatozoa, or their byproducts from migrating, relocating, proliferating, or moving along the path of egress toward the cervix, cervical canal, or uterus. In some examples, the pore size of the filter is approximately 0.2 to 0.45 microns, in order to trap many, most or all bacterial species. In some examples, the pore size of the filter is selected to be smaller than sperm (for example, below 2.5 microns) or bacteria that can cause pathogenic uterine infection, such as *Streptococcus agalactiae* (for example, below 0.5 microns).

In some embodiments, a filter material permeable to gas but not permeable to at least some cellular organisms, microbes, bacteria, viruses, fungi, spermatozoa, or their byproducts is configured to span a path by which gas (for example, air, or gas produced by microbes) can escape during the delivery of the device to the site adjacent to or over the ectocervix, or by which gas (for example, air, or gas produced by microbes) can escape while the device is worn, while the filter prevents migration, relocation, proliferation, or movement of at least some cellular organisms, microbes, bacteria, viruses, fungi, spermatozoa, or their byproducts from moving from a first site in the reproductive system (for example, a site in the anterior vagina) to a second site in the reproductive system (for example, a site in the posterior vagina, cervical canal, or uterus).

In some embodiments, a permeable material—for example, a filter material or a material with wicking properties—bounds at least a portion of a space through which cellular organisms, microbes, bacteria, viruses, fungi, spermatozoa, or their byproducts might migrate, relocate, proliferate, or move from a site in the vagina toward a site adjacent to the cervix or within the cervical canal. The permeable material allows a bacteriostatic, anti-microbial, antiviral, microbicidal, or spermicidal substance stored on a side of the permeable material not bounding the at least a portion of the space to reach the side of the permeable material bounding the at least a portion of a space; in some embodiments. In some embodiments, the permeable material is permeable to the bacteriostatic, antimicrobial, antiviral, microbicidal, or spermicidal substance but not to at least some cellular organisms, microbes, bacteria, bacterial byproducts, viruses, fungi, spermatozoa, or their byproducts; in some embodiments, the permeable material is permeable to most or all cellular organisms, microbes, bacteria, bacterial byproducts, viruses, fungi, spermatozoa, or their byproducts.

In some embodiments, a permeable structure—for example, a filter or fabric—that wicks, transports, allows transport, or allows movement of moisture or egressing material from a first side to a second side more easily than from the second side to the first side is used to allow evacuation of moisture or egressing material from a first site on or within the cervix, within the cervical canal, or in the uterus to a second site in the vagina, while preventing the migration, relocation, proliferation, or movement of cellular organisms, microbes, bacteria, viruses, fungi, spermatozoa, or their byproducts from the second site in the vagina to the first site or other sites on or within the cervix, within the cervical canal, or in the uterus. In some embodiments, the permeable structure features a hydrophilicity gradient between the first and second sides, which causes a capillary pull causing movement of moisture or egressing material from the side with higher hydrophilicity to the side with lower hydrophilicity. In some embodiments, a hydrophobic or hydrophilic coating is applied to a filter material, fabric, or other component to introduce or change a gradient of hydrophilicity.

In some embodiments of the device, a filtering structure is comprised of multiple layers or substructures, which may perform different functions. For example, a filtering structure may have a first layer or substructure featuring a pore size, and a second layer or substructure (that may be coupled to the first layer or substructure) that provides stiffness, strength, or resilience to the filtering structure, or strain relieves or protects the first layer or substructure from damage. In some embodiments, the first layer or substructure may have a smaller pore size than the second layer or substructure.

In some embodiments of the device, a gas, liquid, or gel is contained within a reservoir, the shape of which can adapt to the shape or topography of the anatomy, thereby conforming the device to the anatomy. In some embodiments, liquid or gel within the reservoir hardens after the device is delivered. In some embodiments, conformance of the device to the anatomy ensure proximity of migrating, relocating, proliferating, or moving cellular organisms, microbes, bacteria, viruses, fungi, spermatozoa, or their byproducts to an introduced effect, or to a feature intended to guide cellular organisms, microbes, bacteria, viruses, fungi, spermatozoa, or their byproducts toward a destination other than the cervix, cervical canal, or uterus.

In some embodiments of the device, the device is stabilized by imparting outward force against the vaginal wall, in some instances within the fornix of the vagina. In some embodiments, the device is stabilized by imparting inward force on the ectocervix. In some embodiments, stabilizing force is provided by at least a portion of the device, which at least partially surrounds the ectocervix. A portion of the device providing stabilizing force may be substantially rigid or deformable, and may have different flexibility in different directions or at different sites, for example due to changes in geometry, material stiffness, or construction. In some embodiments, a portion of the device providing stabilizing force may be configured to provide similar force on a vaginal wall or ectocervix with a range of effective diameters or degrees of distension, for example by the incorporation of a linear spring element, which may be encased within a sheath or other structure. In some embodiments, a portion of the device, which may provide stabilizing force, assumes an at least partly spiral or helical shape, which may promote stabilizing force or tissue apposition at a variety of axial locations, along an axis defined by the general direction in which the cervix points. In some embodiments, at least partly curved, spiral, helical, or ring-shaped elements of the device apply force to the ectocervix to prevent cellular organisms, microbes, bacteria, viruses, fungi, spermatozoa, or their byproducts migrating, relocating, proliferating, or moving toward a cervix, cervical canal, or uterus, or provide force to the vaginal wall or the ectocervix to stabilize the device.

Some embodiments of the device feature one or more elastic structures, and two or more surrounding structures. The surrounding structures at least partly circumnavigate the ectocervix, and contact between the surrounding structures and the ectocervix (or force imparted on the ectocervix by the surrounding structure via a device component separating them, which may interact with tissue in a more favorable manner) helps provide a barrier to migration, relocation, proliferation, or movement of cellular organisms, microbes, bacteria, bacterial byproducts, viruses, fungi, spermatozoa, or their byproducts. One or more of the surrounding structures may be deformable or expandable, to accommodate different ectocervical dimensions. The elastic structures connect at least two surrounding structures, which may be positioned at different axial locations, along an axis defined by the general direction in which the cervix points, and act to maintain apposition between a surrounding structure (or a device component separating the surrounding structure from the ectocervix, which may interact with tissue in a more favorable manner) and the ectocervix, for example by pulling the surrounding structure in a direction of increasing ectocervical diameter. In some embodiments, a material connecting surrounding structures partially bounds a volume, further bounded by the ectocervix and in some embodiments, the surrounding structures, in which an antibacterial, antiviral, or spermicidal agent may be contained, or an introduced effect is delivered, or a path guiding cellular organisms, microbes, bacteria, viruses, fungi, spermatozoa, or their byproducts away from the cervix, cervical canal, or uterus is provided.

In some embodiments of the device, multiple surrounding structures which at least partly circumnavigate the ectocervix are connected by a material, which may be elastic, which ensures a minimum or maximum distance between connection sites when the device is positioned over, around, or adjacent to an ectocervix. The multiple surrounding structures may impart force on the ectocervix, which may act to stabilize the device and/or to create one or more barriers to migration, relocation, proliferation, or movement of cellular organisms, microbes, bacteria, viruses, fungi, spermatozoa, or their byproducts past or around the one or more barriers. In some embodiments of the device, the surrounding structures are concentrated near the posterior ectocervix, to prevent bacteria from migrating, relocating, proliferating, or moving onto or into a larger portion of the ectocervix. In some embodiments, the material connecting the surrounding structures is tensioned in at least one direction, for example due to interference between one or more of the surrounding structures and the ectocervix, and in some embodiments, this promotes closer proximity between the connecting material and ectocervical tissue. In some embodiments, a region bounded at least in part by the ectocervical tissue and the connecting material is at least partly filled with a substance that is microbicidal or spermicidal, or contains a therapeutic agent, or contains an antiviral agent.

In some embodiments, a stabilizing structure at or near a posterior region of the device (for example, a structure circumnavigating the ectocervix) stabilizes the device by imparting pressure on the vaginal wall or the ectocervical surface, at an interface between the device and tissue that restricts migration, relocation, proliferation, or movement of bacteria, bacterial byproducts, viruses, or sperm between the stabilizing structure and tissue and toward the cervical canal or uterus. In some embodiments, a component of the device covers, partly or fully, the ectocervix between the stabilizing structure and a gatekeeping structure, located near or over the cervical opening; in some embodiments, this component of the device is partly or fully stretchable, to pull the gatekeeping structure to a preferred position relative to the cervical opening. The gatekeeping structure prevents direct contact between ectocervical tissue and the vaginal wall, prevents accumulation within the device of egressing materials traveling from the cervix or uterus toward or into the vagina, and has one or more features to prevent migration, relocation, proliferation, or movement of cellular organisms, microbes, bacteria, viruses, fungi, spermatozoa, or their byproducts from the vagina toward or into the cervix, cervical canal, or uterus. In some embodiments, the gatekeeping structure delivers an introduced effect to cellular organisms, microbes, bacteria, viruses, fungi, spermatozoa, or their byproducts migrating, relocating, proliferating, or moving from the vagina toward or into the cervix, cervical canal, or uterus. In some embodiments, the gatekeeping structure delivers an introduced effect to egressing materials traveling from the cervix or uterus toward or into the vagina, to prevent the egressing materials from acting as a medium for cellular organisms, microbes, bacteria, viruses, fungi, spermatozoa, or their byproducts to migrate, relocate, proliferate, or move from the vagina toward or into the cervix, cervical canal, or uterus.

In some embodiments of the device, Nitinol is used to achieve a desired configuration of the device relative to the ectocervix or the vaginal wall, or to achieve a desired force between the device and the ectocervix or vaginal wall.

In some embodiments of the device, multiple cap-like components are nested, each covering at least a portion of the ectocervix. The multiple cap-like components may be connected in a manner that promotes a desired position of one or more of them.

In some embodiments, the device is held in position in part or whole by a vacuum formed between the device and ectocervical tissue. In some embodiments, a vacuum is formed in a space or a potential space between the device and one or more of ectocervical tissue or the vaginal wall, while a vacuum is not formed in a space or potential space bounded at least in part by the device and one or more of the cervical mucus plug and the endocervical canal. In some embodiments of the device, a vacuum is not formed in a space or a potential space by providing a vent between the space or potential space and a site (for example, the vagina anterior to the device) with a pressure considered neither pressurized or in vacuum compared with the space or potential space.

In some embodiments, a surface topography is used to help maintain a desired position of the device over, around, or within the proximity of an ectocervix. In some embodiments, one or more recessions on the device create one or more spaces in which a vacuum is formed between the device and cervical or vaginal tissue, which may help maintain a preferred position of the device.

In some embodiments depressions on a surface of the device and ectocervical or vaginal tissue bound one or more volumes where a vacuum forms upon or after application of the device. In some embodiments, vacuum formed in these one or more volumes maintain or help maintain a desired position of the device relative to the ectocervix. In some embodiments, these one or more volumes are continuous with a valve, which preferentially allows outflow of trapped liquids or gases from the one or more volumes. In some embodiments, motion of a wearer of the device contributes to the pumping of liquids or gases from the one or more volumes.

In some embodiments, the device is configured to gradually change shape to accommodate anatomical changes, such as changes to the morphology or stiffness of a cervix. For example, the device may be constructed of a material— for example, a viscoelastic material—that undergoes measurable creep under a sustained load.

In some embodiments, the device is delivered using a delivery system that enables or helps enable proper fitting of the device. In some embodiments, the delivery system is integrated with or used with a speculum and/or a visualization tool.

In some embodiments, at least part of the device is custom-fitted to the wearer. In some embodiments, a non-custom-fitted component of the device is coupled to a custom-fitted component of the device to form part or all of the device. In some embodiments, measurements of the vagina or cervix of the wearer are taken, and at least a portion of the device is 3D printed to provide a custom fit.

In some embodiments, one or more valves are configured to preferentially permit movement of egressing material from a first site to a second site, while preventing movement of cellular organisms, microbes, bacteria, viruses, fungi, spermatozoa, or their byproducts from the second site to the first site. In some embodiments the one or more valves constitute a path of egress that allows the egressing material, arriving from the cervix, cervical canal, uterus, or a region bounded at least in part by the device and the vaginal wall or a portion of the cervix (for example, a region bounded in part by the endocervical canal), to reach a site in the vagina more easily, more quickly, or under less pressure, than if the path of egress was not present. In some embodiments, the one or more valves are placed in parallel, such that the egressing material moving from the cervix, cervical canal, uterus, or a region bounded at least in part by the device and the vaginal wall or a portion of the cervix (for example, a region bounded in part by the endocervical canal) could feasibly pass through any one of multiple valves to the site in the vagina. In some embodiments, the one or more valves are placed in series, such that the egressing material moving from the cervix, cervical canal, uterus, or a region bounded at least in part by the device and the vaginal wall or a portion of the cervix (for example, a region bounded in part by the endocervical canal) may pass, is likely to pass, or must pass through at least two valves in order to reach the site in the vagina.

In some embodiments, valves are configured such that both cannot be, or are unlikely to be, opened simultaneously. For example, an element of a first valve that displaces when the first valve opens could, upon displacement, act to close, move toward closed or ensure closed, a second valve. In another example, the pressure at a given site required to open a second valve could exceed a pressure sufficient at the given site to keep a first valve closed, for example by pressing on one or more surfaces of the first valve, said first valve in some embodiments comprising an umbrella valve, a flapper valve, or a duck-billed valve. In some embodiments, configuring valves such that both cannot be, or are unlikely to be, opened simultaneously may prevent migration, relocation, proliferation, or movement of cellular organisms, microbes, bacteria, viruses, fungi, spermatozoa, or their byproducts from a location downstream from the second valve (where downstream is defined as the direction in which a valve is designed to permit flow) to a location upstream of the first valve, for example by preventing cellular organisms, microbes, bacteria, viruses, fungi, spermatozoa, or their byproducts from migrating, relocating, proliferating, or moving upstream of the first valve before an introduced effect provided between the first and second valves has occurred. In some embodiments, a distance or path between valves—for example, an extended path—is chosen to ensure sufficient exposure of cellular organisms, microbes, bacteria, viruses, fungi, spermatozoa, or their byproducts to an introduced effect provided between valves.

It should be understood that the a variety of valve types could be employed in the inventions described herein, including but not limited to ball valves, butterfly valves, choke valves, diaphragm or membrane valves, gate valves, globe valves, knife valves, needle valves, pinch valves, piston valves, plug valves, solenoid valves, spool valves, check valves, barbed check valves, flow control valves, poppet valves, pressure reducing valves, thermal expansion valves, relief valves, sampling valves, stopcock valves, cock valves, duckbill valves, flapper valves, leaf valves. In some embodiments, two or more different types of valves may be used in a single device.

In some embodiments, one or more valves are formed by a slit-like feature in a member, which opens as a result of a pressure differential across the slit-like feature. In some embodiments, the one or more valves formed by a slit-like feature in a member are configured such that the pressure differential required to open the valve when pressure is higher on a first side than on a second side of the member, is lower than the pressure differential required to open the valve when pressure is higher on the second side than on the first side of the member.

In some embodiments, a passageway is provided for passage of egressing materials that contains one or more compliant members configured to at least partially obstruct the passageway unless pushed open by the egressing materials. In some embodiments, the one or more compliant members are attached to a supporting member that extends along at least part of the passageway, which in some embodiments creates a brush-like feature. In some embodiments, the one or more compliant members and the supporting member are essentially different portions of the same continuous structure. In some embodiments, the compliant members are disc-like, and in some embodiments, the compliant members are bristle-like.

In some embodiments of the device, one or more magnets may be used to maintain apposition between a portion of the device and the ectocervix. In some embodiments of the device, one or more magnets may be used to achieve the opening or closing, or to maintain an opened or closed state, of a valve.

In some embodiments, egressing material is collected in the device while the device is worn, and removed from the device after the device is removed from the wearer. In some embodiments, the device is cleaned or sterilized after removal, prior to being worn again by a wearer. In some embodiments, the egressing material is removed from the device while the device is worn by the wearer. In some embodiments, the egressing material is discarded with the device after removal from wearer. In some embodiments, the device has a feature used to aid in the removal of the egressing material or to aid in cleaning. For example, the device may have a feature configured to accommodate or attach to a syringe or hose used to inject gas or liquid to clean or evacuate a region of the device. In some embodiments, the feature may be configured to accommodate or attach to a syringe with a "Luer Lock" or "Luer slip" fitting. The device may also have a feature from which injected gas or liquid as well as egressing materials are ejected, and a hose, a tube-like feature, or a syringe may be connected to this feature, and in some embodiments used to aspirate the egressing material. In some embodiments, the egressing materials are evaluated to determine a condition or status, including but not limited to one or more of the following: likelihood of premature birth, stillbirth, miscarriage, or another condition; characteristics of cervical mucus; rupture of an amniotic membrane; presence, amount or proportion of blood; status of a fetus, including viability; presence, amount, or proportion of fetal fibronectin.

In some embodiments, the illumination or non-illumination of a light indicates whether an introduced effect, such as light, is being delivered to a region, and/or indicates a level of energy, or a range of levels of energy, remaining in an energy source, such as a battery. In some embodiments, the indicating light has been filtered or reflected, such that light to which a viewer of the indicating light or wearer of the device is exposed has a different wavelength and/or intensity as the light prior to the filtering or reflection. In some embodiments, the light to which the viewer is exposed has a wavelength and/or intensity, or other characteristic that is believed to pose less risk to the viewer of the light or wearer of the device than the light prior to the filtering or reflection. In some embodiments, the indicating light originates from a light providing an introduced effect; in some embodiments, the indicating light shares a power source with the light providing an introduced effect.

In some embodiments, a transmission (for example, a radio transmission or a Bluetooth transmission) provides indication whether an introduced effect, such as light, is being delivered to a region, and/or indicates a level of energy, or a range of levels of energy, remaining in an energy source, such as a battery.

In some embodiments, at least a portion of the device is configured to change position, shape, or appearance upon one or more events or changes of status. The one or more events or change of status could occur due to the arrival or accumulation of egressing material. In some embodiments, a chemical reaction occurs between an egressing material and a component of the device—for example, a coating on at least a portion of the device—that produces a visual effect, such as a change of color that in some embodiments provides indication that the egressing material is or was present. In some embodiments, arrival or accumulation of egressing material results in force or pressure on at least a portion of the device which causes the portion of the device to distend, displace, or otherwise change position, and the distension, displacement, or change of position provides a visible or tactile indication to a person of the arrival or accumulation of the egressing material.

As described herein, various portions of the device may have a convex surface and/or a concave surface. In some embodiments, a portion of a containing element of the device could move from a first position to a second position, due to force or pressure imparted by egressing material arriving from a site in the uterus, cervix, cervical canal, or vagina. For example, a convex surface on a portion of the device could switch to a concave surface, due to force or pressure on the previously convex surface from the egressing material. In some embodiments, another side of the portion of the device is switched from a concave shape to a convex shape due to the force or pressure on the previously convex surface, which may be felt or viewed by a wearer of the device or by an examiner of the device. In some embodiments, the change in position or shape of a surface results in a reduction in force or pressure imparted on the surface. In some embodiments, the change in position or shape of the surface remains after the force or pressure on the surface decreases to an amount lower than that originally required to cause the change in position or shape. In some embodiments, the wearer may feel that a portion of a containing element of the device has moved, or may feel the movement itself, while wearing the device.

In some embodiments, egressing material may be viewed on or through the device. In some embodiments, a translucent region provides visibility of egressing material below, on, within, or above the device. In some embodiments, an opening in the device provides line of sight to egressing material below, on, within, or above the device.

In some embodiments, the device is configured to include a recession, wherein an exit for egressing material is located, thereby preventing direct contact between the exit and tissue, such as the vaginal wall. Such a configuration may prevent or reduce continuity (or a continuous volume) of wetness, fluid, or egressing material between the exit and the tissue, including where such continuity might act as a medium for migration, relocation, proliferation, or movement of bacteria, bacterial byproducts, viruses, or sperm from the vagina to the cervix, cervical canal or uterus. In some embodiments, the geometry of the device, including but not limited to the geometry of the exit (including dimensions that affect or determine the size of a drop of egressing material escaping from the exit) or geometry of features that define the contours of the recession, may cause the distance between the exit and tissue to exceed a dimension of a drop of egressing material escaping from the exit, for example, the longest length between any portion of the drop and another portion. In some embodiments of the device, the contours of the recession create leak paths from the recession, such that egressing material, fluids, or air or other gases may escape the space created or defined by the recession, which may prevent or reduce continuity (or the continuous volume) of wetness, fluid, or egressing material between the exit or tissue, or may prevent accumulation of egressing material, fluids, or air in the device or the recession, or may help allow additional egressing material to pass through the exit.

In some embodiments, the device preserves a path of passage for egressing material, while preventing the anterior and posterior lips of the external orifice of the cervix from contacting the posterior vaginal wall.

In some embodiments, motion by a wearer of the device or changes in the anatomy of the wearer (for example, swelling or dilation of a cervix) cause pressure or force on the device that changes the shape, in some embodiments temporarily or intermittently, of at least a portion of the device and causes a desired effect.

In some embodiments, the change of shape changes the pressure in a space within or adjacent to the device, which in some embodiments is continuous with a region, or is a region, in which egressing material once present in or on the uterus, uterine tissue, cervical canal, cervical tissue, posterior vagina, or vaginal tissue are collected, or the space is continuous with a path, or is part of a path, via which egressing material once present in or on the uterus, uterine tissue, cervical canal, cervical tissue, posterior vagina, or vaginal tissue move to a site in the vagina, such as a site anterior to the device, in some embodiments in a manner that amounts to exiting the device. In some embodiments, the space within or adjacent to the device is bounded partly by the device and partly by tissue (for example, cervical or vaginal tissue); in some embodiments, the space or a subset of the space within or adjacent to the device is bounded partly or in whole by a valve.

In some embodiments, the change in the pressure of the space causes the egressing material to preferentially move in a desired direction (for example, further along a path away from the uterus, cervical canal, or uterus; or toward an introduced effect; or into a collection site in the device; or toward a site in the vagina, such as a site anterior to the device; or toward an egress opening in the device). In some embodiments, the change in the pressure of the space causes one or more valves to open or close, and in some embodiments, the egressing material pass through an opened valve. More generally, the change in the pressure may increase the difference in resistance to movement of the egressing material between (a) a first direction away from a site of collection or passage of egressing material and (b) a second direction toward collection or passage of egressing material; in some embodiments, the lower resistance to movement after the change in the pressure is in the direction toward collection or passage of egressing material. In some embodiments, the impact of the changes of shape is that egressing material is moved toward a site of collection or egress, while features such as valves remain closed in the absence of the changes of shape, such that egressing material is moved toward the site of collection or egress while migration, relocation, proliferation, or movement of cellular organisms, microbes, bacteria, viruses, fungi, spermatozoa, or their byproducts from a site in the vagina to a site adjacent to the cervix or in the cervical canal or in the uterus is prevented.

In some embodiments, fluctuations in the force or pressure on the device (for example, fluctuations caused by movement of the wearer or changes in the morphology of the cervix or vagina) cause one or more of the following: (a) cellular organisms, microbes, bacteria, viruses, fungi, spermatozoa, or their byproducts to be pumped along a path that leads away from the cervix or cervical canal, in a direction leading away from the cervix or cervical canal, in some instances eventually reaching the vagina; (b) egressing material to be pumped along a path that leads away from the cervix or cervical canal, in a direction leading away from the cervix or cervical canal, in some instances eventually reaching the vagina; (c) cellular organisms, microbes, bacteria, viruses, fungi, spermatozoa, or their byproducts to be pumped into a collection region contained in the device; (d) egressing material to be pumped into a collection region contained in the device.

In some instances, the movement of egressing material or cellular organisms, microbes, bacteria, viruses, fungi, spermatozoa, or their byproducts caused by changes in shape of the device, which were caused by motion of the wearer of the device, occurs in a space where vents allow ingress of air or fluid into the space as it assumes a larger volume.

In some embodiments, fluctuations in the pressure or force on the device act to maintain the device's position adjacent to or over the ectocervix, due to interactions between the device and the tissue that are biased to promote movement of the device in a direction that causes the ectocervix to be inserted more fully in to the device. In some embodiments, one or more portions of the device interact with tissue such that more force is required to move the device off the ectocervix (or toward a position off the ectocervix) than is required to move the device further over the ectocervix and/or further posterior within the vagina. In some embodiments, a feature is provided that allows a remover of the device to change the interactions so that the device is easier to move off the ectocervix.

In some embodiments, wherein motion by a wearer of the device helps facilitate a desired movement of cellular organisms, microbes, bacteria, viruses, fungi, spermatozoa, or their byproducts or helps facilitate a desired movement of egressing material, the motion is one or more of the following: walking, running, assuming a different body position (e.g., lying down or standing up), sexual activity, pushing of the device to a more posterior position. In some embodiments, pressure or force on the device is imparted by the vaginal wall and/or the ectocervix.

In some embodiments, the device maintains a desired position, or degree of dilation or closure of, the cervix or cervical canal. In some embodiments, the device imparts force on the ectocervix that advantageously positions the ectocervix relative to surrounding anatomical structures, and/or helps maintain a desired amount of dilation of the cervical canal. In some embodiments, the device acts as a pessary. In some embodiments, the same features that function as a pessary also create a barrier to migration, relocation, proliferation, or movement of cellular organisms, microbes, bacteria, bacterial byproducts, viruses, fungi, spermatozoa, or their byproducts, and/or maintain the position of the barrier.

In some embodiments, a current or future wearer of the device is administered antibiotics, probiotics, or another therapy in order to treat an existing infection (for example, an infection present in the reproductive system) and/or prevent an infection. In some embodiments, the antibiotics, probiotics, or another therapy is administered prior to the wearing of the device. In some embodiments, the antibiotics, probiotics, or another therapy are administered during the wearing of the device.

In some embodiments, the device is used along with an intervention to prevent infection of the cervix or uterus from other routes. For example, a wearer of the device may be administered, or instructed to use, a product to treat oral or periodontal infections, which may cause preterm birth, stillbirth, or miscarriage. For example, the wearer may be instructed to use an antiseptic agent (e.g., mouthwash) or another product before and/or during and/or after pregnancy and/or the wearing of the device.

In some embodiments, the device may be available in multiple sizes or configurations, and a wearer may receive a size or configuration based on a cervical measurements, or whether she has previously given birth vaginally. In some embodiments, tools or instructions for cervical measurement are provided to a current or future wearer of the device, and measurements of the cervix taken by the current or former wearer are used to select a size of the device for the current or former wearer.

In some embodiments, the device is packaged in a kit that includes clean or sterile gloves for use by the person applying the device to the ectocervix, which may be the wearer. In some embodiments, separate gloves, or pairs of gloves, are provided for each of one or more of the following steps: measurement of a cervical dimension (for example, cervical diameter); delivery of the device; removal of the device; delivery of a substance into the device; removal of egressing material from the device; attachment of an accessory to aid in the delivery of a substance into the device; detachment of an accessory to aid in the removal of egressing material from the device; delivery of an agent that prepares (for example, cleans) at least a portion of the ectocervical surface prior to delivery of the device.

In some embodiments, the device is packaged in a kit that includes a tool to aid in measuring the cervix. The tool may be used to select a size of the device, or to adjust the size of the device.

In some embodiments, a kit is provided that includes a wearable device and a substance that is bacteriostatic, antimicrobial, antiviral, or spermicidal, or which prevents migration, relocation, proliferation, or movement of cellular organisms, microbes, bacteria, bacterial byproducts, viruses, fungi, spermatozoa, or their byproducts, and a wearer of the device or a healthcare worker is instructed to apply the substance to, or incorporate the substance into, the device. In some embodiments, the application or incorporation occurs prior to the device being worn by the wearer; in some embodiments, the application or incorporation occurs after the device is positioned near an ectocervix of the wearer.

In some embodiments, the device may be removed by a healthcare worker or the wearer, and one or more of the following actions performed: cleaning the device; evacuating egressing material from the device; downloading data from the device; replacing a battery in the device; confirming that an amount of energy remains in a battery; replacing or adding an antibiotic, bacteriostatic, antimicrobial, antiviral, spermicidal, or antifungal agent; replacing the device with an identical device; replacing the device with another device of a more appropriate size; measuring a dimension of the wearer's cervix.

In some embodiments, a kit is provided with multiple devices that are suited for use at different stages in pregnancy or pre-pregnancy. For example, a kit may contain devices in a range of sizes (for example, sized to accommodate a range of cervical sizes), and during pregnancy, a worn device may be replaced with another device of a more suitable size or shape. In some cases, replacement devices of a different size are shipped to users at or just before a scheduled replacement.

In some embodiments, a region of the vagina or cervix is prepared for delivery of the device by one or more of the following: sterilization of a vaginal surface, sterilization of a cervical surface, cleaning of a vaginal surface, cleaning of a cervical surface, drying of a vaginal surface, drying of a cervical surface.

In some embodiments, a woman is determined to be of elevated risk for premature birth (for example, due to one or more of the following: prior premature birth, family history, cervical length, past or current presence of an infection, composition of a vaginal microbiome); a cervical exam is performed (for example, a cervical exam that includes measurement of the cervix, or use of devices or instruments to assess a size or dimension of the cervix; a first device as described herein is delivered; one or more subsequent devices replace prior devices; a last worn device is removed when a milestone (for example, a particular gestational age or a particular cervical size) is reached.

In some embodiments, the device is worn prior to a woman becoming pregnant, in order to prevent migration, relocation, proliferation, or movement of cellular organisms, microbes, bacteria, viruses, fungi, spermatozoa, or their byproducts from the vagina to the cervix, cervical canal, or uterus. In some embodiments, the device is worn to prevent a pregnancy.

In some embodiments, wearers of the device are instructed to place, remove or replace the device (a) upon the initiation of a menstrual period, and/or (b) a specified amount of time before a menstrual period is expected to begin, and/or (c) a specified amount of time after a menstrual period ends, and/or (d) a specified amount of time before or after sexual intercourse, and/or (e) upon detection of bleeding, and/or (f) when remaining battery life drops below a particular level, or reaches zero.

In some instances, use of the device is contraindicated in patients using vaginal pessaries, intrauterine contraceptive devices, or menstrual cups. In some variations, the apparatuses described herein may themselves act as a menstrual cup. Some of the apparatuses described herein may be configured with an openable valve (such as a pinch valve, slit/slit valve, squeeze valve, or other valve) that may be default closed, but may be opened by the user, e.g., by pushing with her finger in order to allow draining out of the device. For example, the apparatus may include a releasable valve that meters a drain for allowing controlled passage of menstrual material trapped by the device.

In some embodiments, the device releases a therapeutic agent; for example, the device may release progesterone, or an agent to prevent or treat an unhealthy state of the vaginal microbiome (such as bacterial vaginosis). In some embodiments, the device releases bacteria, for example, bacteria of the *Lactobacillus* genus, such as *Lactobacillus* crispatus. In some embodiments, the bacteria transition from a first state of metabolic activity (for example, a metabolically inactive state) to a second state of metabolic activity (for example, a more metabolically active state) after the device is place within a reproductive system, for example in response to heat and/or hydration.

In some embodiments, a flow path for egressing materials is continuous with an agent that changes the pH within part or all of the flow path, and/or a region continuous with the flow path, to a pH that repels, attracts, or affects a cellular organism, microbe, bacteria, virus, fungus, or sperm. In some embodiments, a buffer solution is positioned within a channel and evacuated into another channel through which egressing materials pass. In some embodiments, blood or mucus entering a channel push a pH-changing agent into a path for egressing materials, creating a less hospitable environment for cellular organism, microbe, bacteria, virus, fungus, or sperm that might migrate upstream along the path for egressing materials to a site adjacent to cervical or uterine tissue.

In some embodiments of the device, filaments, filamentous strings, or pathways of small cross sectional area are used to prevent cellular organisms, microbes, bacteria, viruses, fungi, spermatozoa, or their byproducts from migrating, relocating, proliferating, or moving toward the cervix, cervical canal, or uterus, for example by guiding cellular organisms, microbes, bacteria, viruses, fungi, spermatozoa, or their byproducts toward an introduced effect or toward the vagina, for example by capillary effect.

In some embodiments of the device, the device is loaded with bacteria characteristic of a health vaginal, cervical, or uterine microbiome, or bacteria that may adversely affect (for example, outcompete) bacteria, bacterial byproducts, viruses, or sperm that would otherwise migrate, relocate, proliferate, or move toward the cervix, cervical canal, or uterus.

In some embodiments of the device, a sensor detects a pH of a region of the vagina, and causes the release of an agent that changes the pH of the region to favor bacteria characteristic of a healthy vaginal microbiome, or to disfavor bacteria that may adversely affect the vaginal microbiome.

In some embodiments of the device, a drug, pharmaceutical, or therapeutic agent is incorporated into, stored within, or released from the device and delivered to a wearer. The drug, pharmaceutical, or therapeutic agent may act to treat a bacterial or viral infection, maintain a healthy microbiome, promote a desired hormonal state, or act as a spermicide.

In some embodiments, an electric charge, for example inherent to constituent materials or produced using a battery, is used to attract, repel, damage, or kill bacteria, bacterial byproducts, viruses, or sperm.

In some embodiments of the device, a feature (for example, a vent) prevents pressurization of the space between the device and the cervical canal. In some embodiments of the device, the feature is altered to a substantially or fully closed configuration (for example, a vent is closed) after delivery of the device, which in some instances may prevent the feature from providing a path for migration, relocation, proliferation, or movement of cellular organisms, microbes, bacteria, bacterial byproducts, viruses, fungi, spermatozoa, or their byproducts.

In some embodiments, the device is constructed in part or whole of non-porous materials, which may prevent accumulation of cellular organisms, microbes, bacteria, viruses, fungi, spermatozoa, or their byproducts on or within the device. In some embodiments, a porous material is used to trap or aggregate cellular organisms, microbes, bacteria, viruses, fungi, spermatozoa, or their byproducts in order to facilitate or prolong exposure of the cellular organisms, microbes, bacteria, viruses, fungi, spermatozoa, or their byproducts to an introduced effect.

In some embodiments, at least part of the device is coated with a dissolvable material, which by dissolving over time, prevents or reduces the accumulation of a biofilm or other matter on the part of the device. In some embodiments, introduced effects prevent or reduce accumulation of a biofilm on a surface of the device.

In some embodiments, the device is worn continuously or nearly continuously for a period exceeding a month to prevent pregnancy, and has one or more features allowing use throughout a menstrual cycle. For example, the device may collect biological materials associated with the menstrual cycle and allow their removal, after which the device may be cleaned or discarded. In another example, the device may allow passage of biological materials associated with the menstrual cycle, while preventing migration, relocation, proliferation, or movement of cellular organisms, microbes, bacteria, viruses, fungi, spermatozoa, or their byproducts from the vagina to the cervix, cervical canal, or uterus.

In some embodiments, introduced effects, such as the provision of light, are battery powered and/or controlled by a circuit board or other electronic circuitry.

In some embodiments, a strap or handle coupled to the device aids in delivery or removal. In some embodiments, a strap or handle is coupled to the device such that a removal force applied to the strap or handle causes the device to pull away from tissue in a peeling motion (in some cases, inverting the device), which in some cases may require less removal force than displacing the device in shear relative to the tissue.

In some embodiments, a proclivity of a cellular organism, microbe, bacteria, virus, fungus, or sperm to migrate toward or along a surface, a corner, a groove, or a concavity, and/or to depart from a surface, corner, groove, or concavity when the surface, corner, groove, or concavity curves sufficiently away from, or does not curve sufficiently toward, the migration path of the cellular organism, microbe, bacteria, virus, fungus, or sperm (and/or the tangent of the migration path), may be exploited to prevent the cellular organism, microbe, bacteria, virus, fungus, or sperm from traveling from a first site to a second site within a human body (such as a first site in a reproductive system to a second site in a reproductive system). In some embodiments, said exploitation may be used to allow passage of fluids in a downstream direction through or around a device (for example, a medical device occupying space in a reproductive system), while preventing or restricting migration of a cellular organism, microbe, bacteria, virus, fungus, or sperm in an upstream direction.

In some embodiments, one or more features along one or more paths of egressing materials are configured such that a cellular organism, microbe, bacteria, virus, fungus, or sperm migrating generally upstream is guided toward a dead end, where its aforementioned proclivity may delay or prevent it from advancing toward a site where egressing fluids enter or encounter the medical device. In some embodiments, the features redirect the cellular organism, microbe, bacteria, virus, fungus, or sperm in a direction that delays or prevents it from advancing toward a site where egressing materials enter or encounter the medical device. In some embodiments, the features redirect the cellular organism, microbe, bacteria, virus, fungus, or sperm toward an introduced effect. In some embodiments, the features prevent or delay the cellular organism, microbe, bacteria, virus, fungus, or sperm from reaching an upstream region of the one or more paths of egressing materials. In some embodiments, the features redirect the cellular organism, microbe, bacteria, virus, fungus, or sperm toward a site outside of the device (for example, to a region of a reproductive system continuous with the vaginal opening).

In some embodiments, multiple features configured to restrict, slow or prevent translocation of cellular organisms, microbes, bacteria, viruses, fungi, or spermatozoa, are placed in series along a potential path of translocation, in order to achieve a desirable or acceptable overall reduction in likelihood of translocation past the multiple features, even when some lower number of features would not achieve a desirable or acceptable overall reduction. In an illustrating example, twelve valves, each allowing no more than 5% of approaching spermatozoa from migrating past, may be placed in series along a path of egress for egressing materials, thus allowing no more than one out of 4,095,999,999, 999,990 spermatozoa to migrate past the series of valves.

In some embodiments, a desired linear flow rate of egressing materials is achieved by narrowing or widening a flow path, by using valve-like elements that open when a pressure differential ensuring a minimum flow rate is reached, by restricting flow with features positioned in the flow path, by using surfaces along flow paths with intentionally high or low friction, or by other means. In some embodiments, a linear flow rate is achieved that is high enough that a cellular organism, microbe, bacteria, virus, fungus, or sperm cannot overcome to achieve net upstream migration. In some embodiments, a linear flow rate is achieved that is lower than the linear flow rate that would optimally orient a flagellum or flagellum-like structure of a cellular organism, microbe, bacteria, or sperm to propel the cellular organism, microbe, bacteria, virus, fungus, or sperm. In some embodiments, the linear flow rate through a valve that results when the valve's opening pressure is reached exceeds the linear flow rate that can be overcome by flagellum-propelled microbes, such as sperm.

In some embodiments, nano-structures, micro-structures, protrusions, or other topographical elements prevent formation or accumulation of biofilms on or within the device, for example by interrupting locations of attachment between adjacent cellular organisms or between cellular organisms and the device.

In some embodiments, nano-structures, micro-structures, protrusions, or other topographical elements are configured to entangle or create drag on flagella or other propelling structures of cellular organisms. For example, nano-structures, micro-structures, protrusions, or other topographical elements may interact with the tail of sperm to slow or prevent migration of the sperm toward a site in the upper female reproductive system. In some embodiments, nano-structures, micro-structures, protrusions, or other topographical elements may create localized flow patterns of egressing materials that cause cellular organisms to migrate away from, or less efficiently toward, a site in the upper reproductive system at which their presence is unwanted. In some embodiments, defining characteristics of nano-structures, micro-structures, protrusions, or other topographical elements may be varied along a potential migration path of cellular organisms, in order to adversely affect a variety of microorganisms.

In some embodiments, a first region of one or more pathways of egress of egressing materials (such as blood or mucus) contains an agent that is microbicidal, antiviral, anti-fungal, spermicidal, and/or an agent changes a characteristic of a solution to which it is added (for example, a buffer). In some embodiments, the first region is evacuated of some of the agent, for example by one of the following mechanisms: egressing materials entering the first region; diffusion; pressurization, created by deformation of the volume containing the agent; pressurization, created by accumulation of egressing materials. In some embodiments, agent evacuated from the first region enters a second region of one or more pathways of egress of egressing materials, wherein the second region is a potential path of unwanted migration of cellular organisms, microbes, bacteria, viruses, fungi, or spermatozoa, for example from a site in a vagina to a site in or adjacent to a cervix or a uterus. In some embodiments, the one or more pathways of egress of egressing materials are configured such that the relative fluid resistance of the pathway containing the first region, compared to flow paths that do not contain the first region, results in a desired concentration of the agent in a region of the one or more pathways where egressing materials and the agent have converged.

In some embodiments, grooves, channels, or concavities along a path of egress lead cellular organisms with a proclivity to migrate toward or along a surface, a corner, a groove, or a concavity, and/or to depart from a surface, corner, groove, or concavity when the surface, corner, groove, or concavity curves sufficiently away from, or does not curve sufficiently toward, the migration path of the cellular organism, microbe, bacteria, virus, fungus, or sperm (and/or the tangent of the migration path), to introduced effects, including lethal effects.

In some embodiments, non-straight features are placed along or within a path of egress which are generally concave toward a downstream direction, such that a cellular organism, microbe, bacteria, virus, fungus, or sperm with a proclivity to migrate toward or along a surface, a corner, a groove, or a concavity, and/or to depart from a surface, corner, groove, or concavity when the surface, corner, groove, or concavity curves sufficiently away from, or does not curve sufficiently toward, the migration path of the cellular organism, microbe, bacteria, virus, fungus, or sperm (and/or the tangent of the migration path) may be redirected from a net-upstream direction along a path of egress to a net-downstream direction. In some embodiments, the non-straight features are arc-shaped.

In some embodiments, a feature with a channel through which egressing materials may pass protrudes into a volume or chamber along a flow path of egressing materials. In some embodiments, the feature is contoured such that cellular organisms, such as sperm, with a proclivity to migrate along a surface, wall, corner, groove, or concavity and to depart from a surface, corner, groove, or concavity when the surface, corner, groove, or concavity curves sufficiently away from, or does not curve sufficiently toward, the migration path of the cellular organism (and/or the tangent of the migration path) are unlikely, when acting according to said proclivities, to enter the channel in the feature. In some embodiments, the surface of the feature curves abruptly enough toward an opening of the channel that the migrating cellular organism does not follow a path along the surface toward the opening of the channel, but migrates into a region of the volume or chamber, from which it may find a new migration path along a surface, wall, corner, groove, or concavity. In some embodiments, multiple volumes or chambers with the feature are configured in series along a flow path for egressing materials.

In some embodiments, an optimal balance is achieved or approached between (a) the length of a potential migration path of cellular organisms, microbes, bacteria, viruses, fungi, or spermatozoa through or around the device; (b) the volume bounded by the device and/or surrounding anatomical structures, through which the potential migration path passes; and (c) the combined volume of (b) and the volume of structures providing for (b), such as structures bounding (b). In particular, it may be desirable that the path of potential migration of cellular organisms, microbes, bacteria, viruses, fungi, or spermatozoa through or around the device is long, in order to prolong exposure of cellular organisms, microbes, bacteria, viruses, fungi, or spermatozoa to adverse effects; and also desirable that the volume of (b) is minimal, so that the residency time of egressing materials in the vagina is not excessively prolonged, which for example could provide a site for unwanted accumulation or proliferation of bacteria or bacterial byproducts; and further desirable that the volume of (c) is minimal, for example to reduce the overall bulk of the device, which could result in wearer discomfort.

In some embodiments, cornered, grooved, channeled, or concave features may add inefficiency to the journey of cellular organisms from a site in the lower vagina to a site adjacent to a cervix or within a cervical canal or uterus. In some embodiments, a wall of a passageway through which egressing materials pass from a first site in the cervical canal to a second site in the lower vagina includes cornered, grooved, channeled, or concave features along or within which some cellular organisms may tend to locate or migrate. In some embodiments, these features may follow circular or helical paths; for example, a passageway with a generally circular cross-section might reveal, if sectioned longitudinally, grooves, channels, or concave features travelling circumferentially, or at an angle within the plane of the wall of the passageway that is not parallel to the general direction of the passageway. In some embodiments, the cornered, grooved, channeled, or concave features guiding the cellular organisms themselves have cornered, grooved, channeled, or concave features into which the cellular may further locate or migrate.

In some embodiments, the tendency of some cellular organisms to migrate along walls, corners, channels, grooves, or concave features may be exploited to turn a cellular organism from migration along a direction within a passageway that is generally toward a cervix, cervical canal, or uterus, to migration along a direction within the passageway that is generally away from a cervix, cervical canal or uterus.

In some embodiments, the device includes a flexible material that partly or fully bounds a chamber that can be partly or fully filled with a material, in order to achieve contact between the flexible material and an anatomical feature, such as the vaginal wall. In some embodiments, this contact promotes interaction between (a) cellular organisms, microbes, bacteria, viruses, fungi, or spermatozoa, and (b) features of the flexible material that prevent unwanted migration of the cellular organisms, microbes, bacteria, viruses, fungi, or spermatozoa. In some embodiments, the features include nano-structures, micro-structures, protrusions, or other topographical elements on a surface of the device configured to damage, trap, or guide in a desired direction cellular organisms, microbes, bacteria, bacterial byproducts, viruses, fungi, spermatozoa, or their byproducts. In some embodiments, the features prevent formation or accumulation of biofilms on or within the device. In some embodiments, the flexible material is shaped to include regions that concentrate force or pressure between the device and the anatomical feature it contacts, creating contact regions that prevent or guide migration of cellular organisms, microbes, bacteria, viruses, fungi, or spermatozoa with increased effectiveness. In some embodiments, at least a portion of the chamber can distend, deform, displace, or translocate away from a vaginal wall, for example as a result of pressure exerted by a vaginal wall. In some embodiments, the chamber may be partly or fully filled with a material prior to placement in a reproductive tract; in some embodiments, the chamber may be partly or fully filled during or after placement.

In some embodiments, a device may be configured such that a path of egress for egressing materials follows a thermal and/or elevational gradient, such that proclivities of viruses or cellular organisms such as sperm to migrate according to such gradients can be exploited to promote migration in a desired direction (for example, downstream along the path of egress). In some embodiments, an upstream direction along the path of egress may decrease in elevation, and/or in temperature (due to body heat and/or an integrated source of cold or heat), along at least part of the path of egress, when a wearer of the device is lying down, standing, sitting, or in another anticipated orientation. In some embodiments, the path of egress may be configured such that across multiple or all anticipated or possible orientations of the wearer of the device, at least a portion of the path of egress requires a virus or cellular organism such as sperm to migrate against one of these proclivities in order to migrate in a direction along the path that leads to the cervix or uterus.

In some embodiments, egressing materials exiting a cervical canal push other egressing materials through or around the device. In some embodiments, a threshold pressurization of egressing materials exiting a cervical canal must be reached to push other egressing materials through or around the device (for example, to open a threshold valve along a path of egress in or along the device).

In some embodiments, one or more entrances and one or more exits of a path of egress around or through a device are configured so that the exit at lowest elevation is always lower than the entrance at lowest elevation, when the device is worn as instructed and the wearer is commonly oriented.

In some embodiments, volumes continuous with a path of egress may be partly or fully filled with gas, gel, or fluid through membranes or valved paths, which may be configured not to allow egressing materials or migrating cellular organisms to pass through them during use. In some embodiments, partly or fully filling the volumes may provide a medium for desired migration of cellular organisms, for example, away from an upstream direction along a path of egress.

In some embodiments, a Luer-locking or Luer-tapered feature is incorporated into the device, to facility delivery of a gas, gel, or fluid. In some embodiments, a kit is provided to a healthcare worker or a wearer of the device that includes a syringe containing a gas, gel, or fluid intended for injection into or through the device prior to and/or after the device is placed in the reproductive system.

In some embodiments, pathways for egressing materials may also act to equalize pressure between regions continuous with an entrance to and exit from the pathways, and/or allow favorable transfer of gases, such as oxygen, between the regions.

In some embodiments, an introduced effect is delivered unevenly along a path of egress. In some embodiments, the uneven delivery prevents the effect, or a degree of the effect, on tissue, fluids, or cellular organisms in a region of the reproductive system. For example, a change to the pH of fluids within the middle portion of a path of egress may be achieved by concentrating exposure to a buffering agent in that region, while avoiding a similar change to the pH of fluids at another region where exposure to the buffering agent is not concentrated.

In some embodiments, an intravaginal device is comprised of a viscoelastic material that can compress under a load imparted by a vaginal wall, while maintaining apposition along a continuous path that circumnavigates the vaginal canal. In some embodiments, the viscoelasticity allows a change of shape that prevents or undoes a buckling of a structure of the device, wherein said buckling could compromise apposition (for example, apposition that is complete along a path circumnavigating the vaginal canal). In some embodiments, a viscoelastic portion of the device does not itself circumnavigate a portion of the vaginal canal, but deforms by an amount sufficient to adapt the unloaded shape of the device to a shape accommodating the vaginal wall.

In some embodiments, one or more structures coupled to or integrated with the device achieve complete or near-complete apposition with the vaginal wall and/or ectocervix along a path that circumnavigates the vaginal canal, the cervical canal, and/or a path for egressing materials exiting, or which have exited, the cervical canal. In some embodiments, these structures are coupled to each other and/or the device and/or the rest of the device by structures configured to carry a tensile load, but not to carry a significant compressive load, or any compressive load at all. In some embodiments, contact between one or more of these structures and the vaginal wall focuses an introduced effect on a path of potential translocation of cellular organisms, microbes, bacteria, viruses, fungi, or spermatozoa. For example: regions between adjacent structures may be filled with an antibacterial, antiviral, or spermicidal agent; structures may be coated with an antibacterial, antiviral, or spermicidal agent; structures may have a texture, such as nanopillars, that traps or damages bacteria, viruses, or sperm.

In some embodiments, an anatomical measurement of the ectocervix or the upper vagina (for example, a diameter, perimeter, or cross-sectional area) is performed, or inferred from a status (for example, whether a woman has given birth vaginally, or remained pregnant for a particular duration), and a device size is selected with a dimension (for example, a diameter, perimeter, or cross-sectional area) corresponding to the anatomical measurement that exceeds the anatomical measurement when in an unloaded state, but which will deform upon placement at an intended site in the vagina to approach the anatomical measurement. In some embodiments, the deformation occurs due to elasticity or viscoelasticity of at least a portion of the device. In some embodiments, a spring-loaded portion of the device can slide relative to another portion of the device, said another portion in some embodiments comprising a channel or groove through which the spring-loaded portion is contained.

In some embodiments, it may be advantageous to fill a volume continuous with a path of egress of egressing materials with a fluid or gel. In some embodiments, the fluid or gel may contain an agent that affects cellular organisms, microbes, bacteria, viruses, fungi, or spermatozoa. In some embodiments, the fluid or gel may provide a medium for cellular organisms, microbes, bacteria, viruses, fungi, or spermatozoa to migrate along a desired path, or in a desired direction (for example, along a path promoted by walls, corners, channels or grooves along with cellular organisms, microbes, bacteria, viruses, fungi, or spermatozoa are inclined to translocate, or off of ledges, ramps, or other features from which cellular organisms, microbes, bacteria, viruses, fungi, or spermatozoa are prone to depart at desired angles). In some embodiments, the fluid or gel is delivered into the volume before the device is introduced to a wearer of the device, for example, by a manufacturer of the device; in some embodiments, the fluid or gel is delivered into the volume by the wearer, or by a healthcare worker providing the device to the wearer and/or participating in the placement of the device at a site in the reproductive system of the wearer. In some embodiments, a vacuum is used to help fluid or gel reach regions within or around the device. In some embodiments, a region within or around the device where fluid or gel is desirably placed are bounded in part by an air permeable structure, such as a membrane or filter, so that air can escape the region as fluid or gel is introduced.

In some embodiments, a fluid or gel occupies a region, channel, or groove bounded in part by tissue (for example, tissue of the vaginal wall). In some embodiments, the fluid or gel has a viscosity that prevents or slows its departure from the region, channel, or groove.

In some embodiments, one or more materials, such as lactic acid, that promote a localized pH or environment favorable to desirable bacteria and/or unfavorable to unwanted microbes or microbial concentrations is configured on, atop, adjacent to, below, beside, and/or within the device. In some embodiments, the one or more materials promote a localized pH or environment that is unfavorable to sperm, and reduces the likelihood of a pregnancy. In some embodiments, the one or more materials are selected from the following list: lactic acid, ascorbic acid, *lactobacillus*, spermicide, copper, iron, ferrous gluconate, ferrous sulfate, ferrous iron, silver, silver ion, silver alloy, copper, copper ion, copper alloy, zinc, zinc alloy, chlorhexidine, chlorhexidine gluconate, iodine, povidone-iodine, octenidine dihydrochloride, polyhexanide, sodium hypochlorite, sodium bicarbonate, hydrogen peroxide, protease inhibitors, lactic acid, citric acid, acetic acid, essential oils, nonoxynol-9, sodium docecyl sulfate, C31G, BufferGel, polyanions, carrageenans, cellulose sulfate, VivaGel, antiretroviral agents, tenofovir, dapivirine, UC-781, glycine, polyclycolide. In some embodiments, the one or more materials line or are otherwise in contact with a channel, mesh, membrane or pathway through which egressing materials may pass in a downstream direction, and through which microbial migration (including migration of sperm) in an upstream direction is undesired.

Any of the apparatuses (e.g., pessary devices, such as cervical caps, etc.) described herein may have an outer sealing surface that is configured as described herein to provide multiple high contact force regions that may be separated by lower (or no-) contact force regions. These regions may be arranged to provide multiple redundant barriers to the passage of sperm and/or microorganisms and/or viruses into the cervical canal. When the device is positioned within the vagina, a path extending along the vaginal wall from the posterior site in the vagina to a more anterior site in the lower vagina, may include alternating regions including spans of contact (high contract force) and spans of non-contact (and/or low contact force). A span of contact may be understood to be a distance along the path, extending proximally to distally along an outside of the device and/or vaginal wall, within which the device imparts contact force on the vaginal wall. A span of non-contact may be understood as a distance along this path within which the device imparts no contact force (or very low contact force) on the vaginal wall. In some embodiments, a span of contact may be a distance of at least 0.75 mm along the proximal-to-distal path, within which the device imparts contact force on the vaginal wall, and a span of non-contact may be a distance of at least 0.75 mm within which the device imparts no (or very low) contact force on the vaginal wall. In some variations, a span of contact may refer to a distance of at least 1.5 mm along the proximal-to-distal path within which the device imparts contact force on the vaginal wall, and a span of non-contact may be a distance of at least 1.5 mm within which the device imparts no (or very low) contact force on the vaginal wall. Alternatively, in some variations, the span of contact may be a distance of about 2.5 mm or less along the proximal-to-distal path within which the device imparts contact force on the vaginal wall, and a span of non-contact may be a distance of at least about 1.5 mm within which the device imparts no (or very low) contact force on the vaginal wall. In some variations, a span of contact is a distance of about 0.75 mm to about 4 mm along the proximal-to-distal path within which the device imparts contact force (relatively higher contact force) on the vaginal wall, and a span of non-contact is a distance of at least about 1.5 mm within which the device imparts no contact force on the vaginal wall.

In some embodiments, line segments connecting the points of highest contact force between adjacent spans (arranged in the proximal-to-distal axis) create one or more angles between adjacent line segments of less than 180 degrees, and in some cases less than 175 degrees, and in some cases less than 170 degrees, said angles facing away from the nearest vaginal wall (e.g., forming a concave surface facing away from the vaginal wall). For example, line segments connecting the points of highest contact force within the first span of contact along the proximal-to-distal path to the point of highest contact force within the second span of contact along the proximal-to-distal path, and line segments connecting the point of highest contact force within the second span of contact along the path to the point of highest contact force within the third span of contact along the path, and so forth, to the point of highest contact force within the most anterior span of contact, each create one or more angles between adjacent line segments of less than 180 degrees, and in some cases less than 175 degrees, and in some cases less than 170 degrees, in which said angles facing away from the nearest vaginal wall; in some embodiments, all of the angles created between adjacent line segments match these angular dimensions. In some embodiments, the path represents a minimum distance traveling along the vaginal wall from a site in the posterior fornices to the lower vagina. The line segments extend generally in the proximal-to-distal direction (within the vagina, when the device is worn).

In some embodiments, the line segments form a line segment path that only increases in distance from the extended main axis of the cervical canal as the line path extends anteriorly within the vagina. In some embodiments, the line segments form a line segment path that first increases in distance from the extended main axis of the cervical canal as the line segment path extends anteriorly within the vagina, then decreases in distance from the extended main axis of the cervical canal, as the line segment path further extends anteriorly within the vagina.

The spans of contact may occur where protrusions, protruding features, elevated features, ridges, augmentations, or bumps are found on the exterior of the device. In some embodiments, spans of non-contact occur where recessions, grooves, trenches, valleys, dimples, and/or depressions are located on the device.

In general, the maximum contact pressure imparted on the tissue along the path by the device with the alternating protrusions, protruding features, elevated features, ridges, augmentations, bumps, recessions, grooves, trenches, valleys, dimples, and/or depressions may exceed the maximum contact pressure (in some cases, by three fold or higher, or in some cases by six fold or higher) that would be imparted on the tissue by a device of similar exterior profile that lacks the alternating protrusions, protruding features, elevated features, ridges, augmentations, bumps, recessions, grooves, trenches, valleys, dimples, or depressions.

The apparatuses described herein may form a barrier having a high fluid pressure threshold required to breach the interface between the apparatus and the vaginal wall. For example, the minimum fluid pressure difference required to breach the interface between the vaginal wall and the device with the alternating protrusions, protruding features, elevated features, ridges, augmentations, bumps, recessions, grooves, trenches, valleys, dimples, and/or depressions may exceed the minimum fluid pressure difference (in some cases, by three fold or higher, e.g., by six fold or higher) than would be required to breach the interface between the vaginal wall and a device of similar exterior profile that lacks the alternating protrusions, protruding features, elevated features, ridges, augmentations, bumps, recessions, grooves, trenches, valleys, dimples, or depressions.

In some embodiments, the height of the protrusions, protruding features, elevated features, ridges, augmentations, or bumps, or the depth of the recessions, grooves, trenches, valleys, dimples, or depressions, limits localized tissue indentation by ensuring that tissue near the site of locally maximized indentation assumes device contact when the locally maximized indentation reaches a given level. In some embodiments, the given level is between 0.5 mm and 3 mm.

Any of the apparatuses described herein (e.g., some or all of the embodiments described herein) may include any of these outer contact dimensions and features as described herein. Thus, any of these devices may be configured so that the outer interface region of the apparatus, including not only one path traveling along the vaginal wall from a site in the posterior fornicies to the lower vagina, but of most or all paths originating in the posterior fornices, or most or all paths originating from a distinct closed path, which circumnavigates the cervical canal or the ectocervix, such as a distinct closed path posterior to the device, are sealed via the alternating higher and lower contact force regions. The dimensions and spacing described herein may provide particularly beneficial sealing and preventing of sperm and/or microorganisms from passing the barrier.

In some embodiments the protrusions, protruding features, elevated features, ridges, augmentations, bumps, recessions, grooves, trenches, valleys, dimples, and/or depressions provide continuous contact between the device and the vaginal wall along a continuous or near-continuous path that circumnavigates the central axis of the vagina. The maximum contact pressure imparted on tissue along the continuous or near-continuous path by the device may exceed the maximum contact pressure (in some cases by three fold or higher, or in some cases by six fold or higher) that would be imparted on the tissue by a device of similar exterior profile that lacks the protrusions, protruding features, elevated features, ridges, augmentations, bumps, recessions, grooves, trenches, valleys, dimples, and/or depressions as described herein.

The minimum fluid pressure difference required to breach the interface between the vaginal wall and the device along the continuous or near-continuous path may exceed (in some cases, by three fold or higher, or in some cases by six fold or higher) the minimum fluid pressure difference that would be required to breach the interface between the vaginal wall and the device along a similarly-located continuous or near-continuous path, were the device of similar exterior profile, but lacking the protrusions, protruding features, elevated features, ridges, augmentations, bumps, recessions, grooves, trenches, valleys, dimples, and/or depressions.

The tissue-interfacing structures described herein may be formed by the protrusions, protruding features, elevated features, ridges, augmentations, bumps, recessions, grooves, trenches, valleys, dimples, and/or depressions. In some embodiments, these tissue-interfacing structures may be compressed, stretched, bent, displaced, swung, buckled, deflected, and/or deformed under loads created by contact forces with tissue. In some embodiments, these tissue-interfacing structures may be configured to prevent circumferential buckling, for example to prevent the creation of gaps between the tissue-interfacing structure and the tissue. For example, a tissue-interfacing structure may be configured such that force imparted on the tissue-interfacing structure by the tissue causes the tissue-interfacing structure to bend or deflect further in a direction in which it is already angled or otherwise biased to bend or deflect; and/or to compress. One or more tissue-interfacing structures may resemble an acutely angled ledge or rim. In some embodiments, one or more tissue-interfacing structures, if pressed by a tissue wall, would (over at least a range of deflections) bend, decreasing the acute angle, compress in a circumferential direction, and/or not buckle in a circumferential direction. The range of deflections may be between 0% to 50%, or even 0% to 80%, of the distance that the tissue-interfacing structure extends from the surrounding device surface or features. In some embodiments, the range of deflections may include deflections likely to arise from contact between the device and tissue. The "span of contact" or "spans of contact" as described above may be substituted with "span of elevated contact force" or "spans of elevated contact force," respectively, and the "span of non-contact" or "spans of non-contact" as described above may be replaced with "span of non-elevated contact force" or "spans of non-elevated contact force," respectively. Within a span of elevated contact force or spans of elevated contact force, the device may impart a maximum contact force on the vaginal wall that is significantly higher (for example, 2 fold or higher, or even 4 fold or higher) than the maximum contact force imparted by the device on the vaginal wall within a span of non-elevated contact force or spans of non-elevated contact force, where the maximum contact force imparted by the device may be zero or non-zero. For the purpose of considering these embodiments, characteristics of a "span of elevated contact force" or "spans of elevated contact force" or a "span of non-elevated contact force" or "spans of non-elevated contact force" may prevail where they contradict characteristics of a "span of contact" or "spans of contact" or a "span of non-contact" or "spans of non-contact" as earlier defined.

Any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An intravaginal barrier device, comprising:
a dome region configured to fit within a vagina, inferior to an ectocervix, and form a space between the dome region and the ectocervix which is continuous with a first end of an open channel to allow fluid from an external os to travel in a first direction around the intravaginal barrier device toward a second end of the open channel and out to a lower vaginal side of the intravaginal barrier device, wherein an exterior surface of the intravaginal barrier device includes a recessed channel that winds around at least a portion of a central axis of the dome region, wherein the exterior surface of the intravaginal barrier device is arranged to contact a vaginal wall such that the recessed channel and the vaginal wall define the open channel when the intravaginal barrier device is in place within the vagina.

2. The intravaginal barrier device of claim 1, wherein the exterior surface includes one or more protruding features configured to contact the vaginal wall, thereby creating the open channel defined by the recessed channel and the vaginal wall when the exterior surface is against the vaginal wall.

3. The intravaginal barrier device of claim 2, wherein the one or more protruding features extend from a convex portion of the exterior surface of the intravaginal barrier device.

4. The intravaginal barrier device of claim 2, wherein sites of contact between the one or more protruding features and the vaginal wall trace a path that is generally concave toward the central axis of the dome region and within a plane containing the central axis.

5. The intravaginal barrier device of claim 2, wherein the one or more protruding features have a helical shape and/or a spiral shape.

6. The intravaginal barrier device of claim 1, wherein the open channel has a wall shape comprising one or more winds, enlargements, recesses, projections, baffles, ramps, turnarounds, cavities, buckets, corners, grooves, or ledges which passively limit travel through the open channel in a second direction that is opposite the first direction or direct travel back towards the lower vaginal side of the intravaginal barrier device.

7. The intravaginal barrier device of claim 1, wherein the open channel is shaped to form a conduit having a wall shape that impedes progress or proliferation of one or more of sperm, microorganisms, viruses, fungi, or their byproducts toward the first end, or directs the one or more of sperm, microorganisms, viruses, fungi, or their byproducts traveling in the open channel from the lower vaginal side of the intravaginal barrier device to travel in the first direction back towards the lower vaginal side of the intravaginal barrier device.

8. The intravaginal barrier device of claim 1, wherein a surface of the intravaginal barrier device or the open channel is configured to include micropillars, nanopillars, or microstructures configured to prevent migration or proliferation of one or more of sperm, microorganisms, viruses, fungi or their byproducts from the lower vaginal side of the intravaginal barrier device to the ectocervix.

9. The intravaginal barrier device of claim 1, wherein the intravaginal barrier device is configured to lack any movable part configured to open, close, or partially obstruct a port, a passageway, or the open channel.

10. The intravaginal barrier device of claim 1, wherein the open channel radiates from the central axis of the dome region.

11. The intravaginal barrier device of claim 6, wherein the open channel is shaped to provide a resistance to fluid flow through the open channel that is greater in the second direction than in the first direction.

12. The intravaginal barrier device of claim 1, wherein the open channel is configured to have a length of 10 to 300 millimeters.

13. The intravaginal barrier device of claim 1, further comprising an antibacterial, antiviral, antifungal, antimicrobial, bacteriostatic, or spermicidal agent.

14. The intravaginal barrier device of claim 1, wherein the intravaginal barrier device is configured to act as a pessary.

15. The intravaginal barrier device of claim 1, wherein the intravaginal barrier device is configured to lack continuous contact with tissue along any closed path circumnavigating a vaginal canal, and is further configured to lack continuous contact with tissue along any closed path circumnavigating any portion of a central axis of a cervical canal that is located within the cervical canal or a cervix.

16. The intravaginal barrier device of claim 1, further comprising a light source configured to damage, kill, cause not to reproduce, immobilize, attract, or repel sperm, microorganisms, viruses, fungi, or their byproducts.

17. The intravaginal barrier device of claim 1, further comprising a valve.

18. The intravaginal barrier device of claim 1, configured to have a generally convex exterior shape where the device interfaces with the vaginal wall.

19. An intravaginal barrier device, comprising:
a dome region configured to fit over an external os of a cervix and form a space between the dome region and the external os that is continuous with a first opening into a channel to allow fluid from the external os to reach a lower vagina after the fluid exits a second opening into the channel;
an outer interface surface including a recessed channel that winds around at least a portion of a central axis of the dome region, wherein the outer interface surface is arranged to contact a vaginal wall such that the recessed channel and the vaginal wall define the channel when the intravaginal barrier device is in place within the vagina;
wherein the channel lacks any valve that opens or closes.

20. An intravaginal barrier device, comprising: a dome region configured to fit over an external os of a cervix and form a space between the dome region and the external os that is continuous with a first end of an open channel to allow fluid from the external os to travel in a first direction around the intravaginal barrier device toward a second end of the open channel and out to a vaginal side of the intravaginal barrier device, wherein an exterior surface of the intravaginal barrier device includes a recessed channel that winds around at least a portion of a central axis of the dome region, wherein the exterior surface of the intravaginal barrier device is arranged to contact a vaginal wall such that the recessed channel and the vaginal wall define the open channel when the intravaginal barrier device is in place within the vagina.

* * * * *